US012806049B2

(12) United States Patent
Yadav et al.

(10) Patent No.: US 12,806,049 B2
(45) Date of Patent: Nov. 24, 2026

(54) DELIVERY HANDLE ARRANGEMENT FOR PROSTHETIC VALVE DELIVERY SYSTEMS

(71) Applicant: MiRus LLC, Marietta, GA (US)

(72) Inventors: Jay Yadav, Atlanta, GA (US); Ken Holloway, Marietta, GA (US); Miheer Joshi, Marietta, GA (US); Angela Rothfuss, Marietta, GA (US); Jorge Jimenez, Marietta, GA (US)

(73) Assignee: MiRus LLC, Marietta, GA (US)

( * ) Notice: Subject to any disclaimer, the term of this patent is extended or adjusted under 35 U.S.C. 154(b) by 0 days.

(21) Appl. No.: 19/572,286

(22) Filed: Mar. 19, 2026

(65) Prior Publication Data

US 2026/0207360 A1 Jul. 23, 2026

Related U.S. Application Data

(63) Continuation-in-part of application No. 30/021,437, filed on Sep. 4, 2025, and a continuation-in-part of application No. 30/021,457, filed on Sep. 4, 2025, and a continuation-in-part of application No. 18/904,796, filed on Oct. 2, 2024, which is a continuation-in-part of application No. 29/851,277, filed on Aug. 26, 2022, now Pat. No. Des. 1,087,336.

(60) Provisional application No. 63/877,017, filed on Sep. 6, 2025, provisional application No. 63/541,938, filed on Oct. 2, 2023.

(51) Int. Cl.

| | |
|---|---|
| ***A61F 2/95*** | (2013.01) |
| ***A61F 2/24*** | (2006.01) |
| *A61M 25/00* | (2006.01) |
| *A61M 25/01* | (2006.01) |

(52) U.S. Cl.

CPC .......... *A61F 2/9517* (2020.05); *A61F 2/2433* (2013.01); *A61M 2025/0042* (2013.01); *A61M 25/0097* (2013.01); *A61M 25/0136* (2013.01)

(58) Field of Classification Search

CPC ........ A61F 2/9517; A61F 2/95; A61F 2/2433; A61F 2/2427; A61F 2/243; A61F 2/2436; A61M 2025/0042; A61M 25/0136; A61M 25/0097

See application file for complete search history.

(56) References Cited

U.S. PATENT DOCUMENTS

| | | | | |
|---|---|---|---|---|
| 2013/0030520 A1* | 1/2013 | Lee | A61F 2/2433 | 623/2.11 |
| 2023/0210658 A1* | 7/2023 | Syed | A61F 2/2433 | 623/2.11 |
| 2024/0285907 A1* | 8/2024 | McGuinn | A61M 25/0136 | |

* cited by examiner

*Primary Examiner* — Dianne Dornbusch

(74) *Attorney, Agent, or Firm* — UB Greensfelder LLP; Brian E. Turung

(57) ABSTRACT

A delivery handle arrangement and system that facilitates the delivery of an expandable medical device to a treatment site, and wherein the delivery handle arrangement includes a housing having an inner core that extends linearly between a proximal end and a distal end of the housing, and wherein the inner core receives a flexible catheter and a balloon catheter that is disposed coaxially within the flexible catheter; an longitudinal adjustment mechanism that is configured to control a position of the balloon catheter relative to the flexible catheter, and wherein the longitudinal adjustment mechanism includes a control knob and a switch that is configured to lock or unlocked the longitudinal adjustment mechanism.

41 Claims, 13 Drawing Sheets

DELIVERY HANDLE ARRANGEMENT FOR PROSTHETIC VALVE DELIVERY SYSTEMS

REFERENCED APPLICATIONS

The present application is a continuation-in-part of U.S. patent application Ser. No. 18/904,796 filed Oct. 2, 2024, which in turn claims the benefit of U.S. Provisional Patent Application Ser. No. 63/541,938 filed on Oct. 2, 2023 and entitled, "Delivery Handle Arrangement for Prosthetic Valve Delivery Systems", the disclosures of which are fully incorporated herein by reference.

The present application is a continuation-in-part of U.S. patent application Ser. No. 18/904,796 filed Oct. 2, 2024, which in turn is a continuation-in-part of U.S. application Ser. No. 29/851,277 filed Aug. 26, 2022, now U.S. Pat. No. D1,087,336 and entitled, "Delivery Handle Device", the disclosures of which are fully incorporated herein by reference.

The present application is a continuation-in-part of United States Design application Ser. Nos. 30/021,457 filed Sep. 4, 2025 and Ser. No. 30/021,437 filed Sep. 4, 2025, both of which are fully incorporated herein by reference.

The present application claims priority to U.S. Provisional Patent Application Ser. No. 63/877,017 filed Sep. 6, 2025, which is fully incorporated herein by reference.

TECHNICAL FIELD

The present disclosure is directed to prosthetic valve replacement system, particularly to devices, systems, and methods for transcatheter delivery of expandable prosthetic valves, and more particularly to a delivery handle arrangement for an expandable prosthetic valve.

BACKGROUND OF DISCLOSURE

Many cardiovascular devices such as expandable heart valves are inserted into a patient via the patient's vascular system and then expanded at the treatment site. These devices are typically crimped onto catheter prior to insertion into a patient. Medical devices such as transcatheter aortic valves (TAVs) represent a significant advancement in prosthetic valve technology. TAVs bring the benefit of heart valve replacement to patients that would otherwise not be operated on. Transcatheter aortic valve replacement (TAVR) can be used to treat aortic valve stenosis in patients who are classified as high-risk for open heart surgical aortic valve replacement (SAVR). Non-limiting TAVs are disclosed in U.S. Pat. Nos. 5,411,522; 6,730,118; 10,729,543; 10,820,993; 10,856,970; 10,869,761; 10,952,852; 10,980,632; 10,980,633; 12,383,399 and US Pub. No. 2020/0405482, all of which are incorporated fully herein by reference.

A TAV is designed to be compressed into a small diameter catheter, remotely placed within a patient's diseased aortic valve to take over the function of the native valve. Some TAVs are balloon-expandable, while others are self-expandable. In both cases, the TAVs are deployed within a calcified native valve that is forced permanently open and becomes the surface against which the stent is held in place by friction. TAVs can also be used to replace failing bioprosthetic or transcatheter valves, commonly known as a valve in valve procedure. Major TAVR advantages to the traditional surgical approaches include refraining cardiopulmonary bypass and/or aortic cross-clamping and sternotomy that significantly reduces patients' morbidity.

However, several complications are associated with current TAV devices, such as mispositioning, crimp-induced leaflet damage, paravalvular leak, thrombosis, conduction abnormalities, and prosthesis-patient mismatch. These complications are potentially associated with the calcification landscape of the native valve, geometric and mechanical properties of the aortic root, blood biochemistry and coagulability associated with the patient, and concomitant conditions such as hypertension, coronary artery disease, heart failure, etc.

TAVR involves delivery, deployment, and implantation of a crimped, stented valve within a diseased aortic valve or degenerated bioprosthesis. Prosthetic valves that are collapsible can be delivered into a patient via a tube-like delivery apparatus such as a catheter, a trocar, a laparoscopic instrument, or the like, thus avoiding more invasive procedures such as full open-chest, open-heart surgery.

When the collapsed prosthetic valve has reached the desired treatment site in the patient (e.g., patient's heart valve that is to be replaced by the prosthetic valve), the prosthetic valve can be expanded in the treatment site.

In conventional delivery systems for prosthetic valves, after the prosthetic valve is positioned at the treatment site, the positioning of the prosthetic valve may need to be adjusted prior to expansion of the prosthetic valve at the treatment site. Many delivery devices can adjust the linear position of the prosthetic valve in the treatment site, but cannot both linearly and angularly adjust the prosthetic valve at the treatment site. Such angular adjustment can be beneficial to adjust the leaflet system of the prosthetic valve in the treatment site to improve the effectiveness of the prosthetic valve after deployment at the treatment site.

There therefore is a need for further improvements to the devices, systems, and methods for transcatheter delivery of collapsible prosthetic valves.

SUMMARY OF DISCLOSURE

The present disclosure is directed to prosthetic valve replacement, particularly to devices, systems, and methods for transcatheter delivery of expandable medical device, and more particularly to a delivery handle arrangement for use with and delivery of expandable medical device. In particular, the present non-limiting disclosure is directed to a delivery handle arrangement that facilitates the delivery of an expandable medical device to a treatment site (e.g., stent, TAV, heart valve, etc.). However, it will be appreciated that the delivery handle arrangement in accordance with the present disclosure can be used to delivery other types of medical devices to a treatment site.

In one non-limiting aspect of the present disclosure, the delivery handle arrangement includes a housing having an inner core that extends linearly between a proximal end and a distal end of the housing. The inner core is configured to be connected to and/or receive a portion of a flexible catheter and optionally receive a portion of an expandable balloon catheter that is disposed coaxially with the flexible catheter. The delivery handle arrangement includes a longitudinal adjustment mechanism that is configured to control a position of the distal end or end region of the balloon catheter (which distal end or end region of the balloon catheter includes a one or more of an inflatable balloon, stent, heart valve, LAA (left atrial appendage) closure device, etc. so as to properly position the end or end region of the balloon catheter and medical device at the treatment site. In one non-limiting configuration, the longitudinal adjustment mechanism is connected to the catheter and is configured to move the complete catheter longitudinally relative to the housing. In another non-limiting configuration, the longitudinal adjustment mechanism is connected to the balloon catheter so that balloon catheter is moveable by the longitudinal adjustment mechanism relative to the outer body of the catheter. In one non-limiting configuration, the longitudinal adjustment mechanism can include a control knob that optionally has a plurality of threads; a shaft (e.g., an optional threaded shaft, etc.) that is configured to translate linearly within the housing; and an optional switch, latch, etc. that is configured to lock and/or unlocked the fine tuning feature or fine adjustment feature of the longitudinal adjustment mechanism.

In another and/or alternative aspect of the present disclosure, there is provided a delivery system that includes a delivery handle, wherein the delivery handle includes a housing that optionally has a flex adjustment mechanism that includes a flex knob or flex adjustor. In one non-limiting embodiment, flex knob or flex adjustor is movably connected to the housing of the delivery handle (e.g., rotatable connected to the housing of the delivery handle, slidably connected to the housing of the delivery handle, etc.). In another and/or alternative embodiment, the flex knob or flex adjustor can include a body portion (e.g., threaded body portion, etc.) that is partially or fully positioned in the body cavity of the housing. The flex knob or flex adjustor can coupled (e.g., threadedly coupled, slidably coupled, etc.) to an flex insert and/or flex actuator (e.g., threaded flex insert and/or flex actuator, etc.), and wherein the flex insert and/or flex actuator is partially or fully contained within the housing, and wherein the flex knob or flex adjustor is configured to cause the flex insert and/or flex actuator to move (e.g., rotate, slide, etc.) within the housing during movement of the flex knob or flex adjustor. In one non-limiting configuration, the flex knob or flex adjustor is configured to engage a flex insert and/or flex actuator (e.g., threaded flex insert, threaded flex actuator, etc.) and to cause the flex insert and/or flex actuator to move during movement of the flex knob or flex adjustor. In another non-limiting configuration, the flex insert and/or flex actuator is configured to move within the housing (e.g., move along a longitudinal axis of the housing, etc.) during movement of the flex knob or flex adjustor. In another non-limiting configuration, the flex insert and/or flex actuator is connected to one end of a wire member, and which wire member is connected at an opposite end to the flexible catheter. The type of connection used to connect the wire member to the flexible catheter and to the flex insert and/or flex actuator is non-limiting (e.g., clamp, weld, friction connection, adhesive, melted connection, etc.). In another non-limiting embodiment, rotation of the flex knob in a first direction causes the flex insert and/or flex actuator to translate linearly along the longitudinal axis of the housing away from the distal end of the housing towards the proximal end of the housing, and wherein the wire member pulls the distal end or distal region of the flexible catheter or the balloon catheter to cause bending or flexing or increased bending or flexing of the distal region of the flexible catheter or the balloon catheter at a predetermined angle and/or orientation, and rotation of the flex knob in a second opposite direction causes the flex insert and/or flex actuator to translate linearly along the longitudinal axis of the housing away from the proximal end of the housing towards the distal end of the housing, and wherein the wire member unpulls the distal end or distal region of the flexible catheter or the balloon catheter to cause less bending or less flexing or no bending or no flexing of the distal region of the flexible catheter or the balloon catheter.

In another and/or alternative non-limiting aspect of the present disclosure, the delivery handle arrangement optionally includes a flex adjustment mechanism that has one or more flex indicators to indicate an amount of flex of the catheter or the balloon catheter at the distal region of the catheter or the balloon catheter. In one specific arrangement, the flex indicator includes a needle, electronic counter or indicator to indicate to a user the degree to indicate an amount of flex of the catheter or the balloon catheter at the distal region of the catheter or the balloon catheter. The flex indicator can optionally include numbers, letters, bars, sloped graphics, shapes, or other markings to provide the user additional information on the degree or amount of flex in the flexible catheter or balloon catheter. In one specific configuration, the flex indicator includes a needle, and wherein the needle is configured to translate along the flex insert and/or flex actuator (e.g., threaded flex insert and/or flex actuator, etc.) to indicate to a user the degree or amount of flex or bend in the catheter or the balloon catheter. In another and/or alternative non-limiting embodiment, the delivery handle arrangement optionally includes a flex indicator and flex indicator window. The flex indicator can optionally be configured to move within the flex indicator window to indicate the degree of flex at the distal region of the catheter and/or balloon catheter. The flex indicator and flex indicator window can be part of the optional flex adjustment mechanism of the delivery handle. Transcatheter Aortic Valve Replacement (TAVR) involves delivering a prosthetic aortic valve endovascularly to the native aortic annulus using a delivery system. For balloon expandable valves, the delivery system is commonly comprised of a balloon catheter which is used to expand the valve, a catheter which is used to guide the medical device through the vascular system, and a handle which serves as the user interface for the catheter and medical device. Typically, access to the patient's arterial system is via the common femoral artery and the delivery system is advanced through the descending aorta, around the aortic arch to the aortic annulus. The aortic arch has significant curvature to it which requires the delivery system to navigate across without damaging the vessel. Additionally, the aortic root can often be very angled (>70°) making delivery of the valve challenging. Flexing of the distal region of catheter and/or balloon catheter during advancement around the aortic arch can be used to reduce system insertional forces, thereby minimizing arterial wall stress and mitigating risk of vascular injury. Once the medical device and catheter has reached the aortic annulus, the ability to being able to controllably flex the distal region of the catheter and/or balloon catheter can aid in ensuring the valve is positioned coaxial to the aortic root, thereby optimizing valve delivery. In accordance with the present disclosure, flexion of the distal region of the catheter and/or balloon catheter can be accomplished by optionally placing a pull ring within the region of the catheter and wherein a pull wire is connected to the pull ring. The pull wire can optionally be encased within the catheter and runs along a portion or all of the length of the catheter and to the delivery handle. To flex or bend the distal region of the catheter, the pull wire is pulled, which in turn causes the tensile force to be applied to the pull ring, which in turn causes the distal region of the catheter to deflect and bend in a desired direction. The direction of the flex and bend can be controlled by the location of the pull ring to the pull wire connection and the configuration of the catheter.

In another and/or alternative non-limiting aspect of the present disclosure, the delivery handle arrangement optionally includes a rotational mechanism that is configured to rotate the catheter or the balloon catheter, which in turn causes rotation of the medical device on the catheter or balloon catheter. In one non-limiting embodiment, the rotational mechanism optionally includes an alignment knob that is coupled to a shaft (e.g., the threaded shaft) of the longitudinal adjustment mechanism; and wherein rotation of the alignment knob in a first direction causes rotation of the catheter or rotation of the balloon catheter relative to the catheter.

In another and/or alternative non-limiting aspect of the present disclosure, the delivery handle arrangement optionally includes a control knob that has a first stop position and a second stop position, and wherein there is optionally provided a switch that is positioned between and moveable between the first stop position and the second stop position.

In another and/or alternative non-limiting aspect of the present disclosure, the switch optionally includes a channel having a first stop and a second stop. The first stop optionally has a different width or height from the second stop (e.g., the first stop has a greater width or height than the second stop). In another non-limiting embodiment, the switch optionally has a substantially circular cross-sectional shape; however, other shapes can be used. The switch is used to a) engage the fine tuning feature or fine adjustment feature of the longitudinal adjustment mechanism when the switch in the first position or locked position, and b) disengage the fine tuning feature or fine adjustment feature of the longitudinal adjustment mechanism when the switch in the second position or unlocked position. The fine tuning feature or fine adjustment feature results in small and precise longitudinal movement of the hypotube or shaft in the body of the housing so as to finely and accurately longitudinally move the medical device at a treatment site for proper positioning of the medical device at the treatment site.

In another and/or alternative non-limiting aspect of the present disclosure, when the fine tuning feature or fine adjustment feature is in the locked position, a collet is optionally compressed on the hypotube or shaft of the delivery handle, thus preventing rapid forward and backward movement of the balloon catheter relative to the catheter. In one non-limiting configuration, when the fine tuning feature or fine adjustment feature is in the locked position, the turning the positioning wheel causes the hypotube or shaft of the delivery handle to move forward and backward. In another non-limiting configuration, when the positioning lock is in the unlocked position, the hypotube or shaft of the delivery handle can be freely slid forwards or backwards. As such, when the fine tuning feature or fine adjustment feature is in the locked position, the control knob can be used to finely and accurately longitudinally move the medical device on the balloon catheter; and when the fine tuning feature or fine adjustment feature is in the unlocked position, the fine longitudinal adjustment feature is inactive, and the shaft or hypotube can be moved back and forth along longitudinal axis of catheter at a larger distance than when the fine longitudinal adjustment feature is in the locked position. The back portion of the handle (e.g., portion of the handle connected to the fluid tubes) can be freely moved forward and backward when the fine longitudinal adjustment feature is in the unlocked position for quick initial positioning of the inflatable balloon or medical device (TAV) connected to the inflatable balloon at the treatment site, and thereafter, the fine longitudinal adjustment feature can be positioned in the locked position for fine longitudinal adjustment or positioning of the inflatable balloon or medical device (TAV) connected to the inflatable balloon at the treatment site.

In another and/or alternative non-limiting aspect of the present disclosure, the delivery handle arrangement is optionally configured that when the switch is in the first or locked position, the catch of the longitudinal adjustment mechanism optionally moves into engagement with the shaft or hypotube or is moved into engagement with an insert (e.g., threaded insert, gear, etc.) and/or causes the insert to move into engagement with the hypotube or shaft (e.g., threads on the shaft, etc.). In one non-limiting embodiment, rotation of the control knob in a first direction, when the switch in the first position or locked position, causes the hypotube or shaft to translate or move linearly from the proximal end towards the distal end within the housing, and wherein rotation of the control knob in a second direction, when the switch in the first position or locked position, causes the hypotube or shaft to translate linearly from the distal end towards the proximal end.

In another and/or alternative non-limiting aspect of the present disclosure, the delivery handle arrangement is optionally configured that when the switch is in the second or unlocked position, the catch is disengages from the hypotube or shaft or causes the insert (e.g., threaded insert, gear, etc.) to disengage from the hypotube or shaft, and the hypotube or shaft can optionally be freely moved linearly from the proximal end towards the distal end within the housing without having to rotate the control knob. In one non-limiting configuration, when the switch in the first position or locked position, the hypotube or shaft can only be moved linearly between the proximal end towards the distal end within the housing when the control knob is rotated. In one non-limiting embodiment, the alignment knob of the rotational mechanism is configured to be moved or slid along the longitudinal length of the housing so as to advance the hypotube or shaft towards the distal end of the housing or to retreat the hypotube or shaft away from the distal end of the housing when the switch is in the second or unlocked position.

In another and/or alternative non-limiting aspect of the present disclosure, the longitudinal adjustment mechanism includes a switch that is movable between a locked and unlocked position. In one non-limiting embodiment, the movement of the switch between the locked and unlocked position is limited by a first stop position and second stop position on the housing, and wherein the switch is movable along the longitudinal axis of the housing, and wherein the switch optionally rotates with the control knob when the control knob is rotated to fine adjust the movement of the hypotube or shaft in the housing when the switch is in the locked position. In another non-limiting embodiment, the switch is a press button switch, and wherein the switch optionally rotates with the control knob when the control knob is rotated to fine adjust the movement of the hypotube or shaft in the housing when the switch is in the locked position. In another non-limiting embodiment, the switch is movable about the longitudinal axis of the housing, and wherein the switch optionally rotates with the control knob when the control knob is rotated to fine adjust the movement of the hypotube or shaft in the housing when the switch is in the locked position. In another non-limiting embodiment, the switch rotates or pivots about a point on the control knob, and wherein the switch optionally rotates with the control knob when the control knob is rotated to fine adjust the movement of the hypotube or shaft in the housing when the switch is in the locked position. As can be appreciated, other type of switches can be used (e.g., electronic switch, etc.).

In another and/or alternative non-limiting aspect of the present disclosure, the delivery handle arrangement optionally includes a luer tree coupled to the alignment knob or hypotube. The luer tree optionally includes one or more of a) a flush port, b) a guidewire lumen that is configured to receive a guidewire, and/or c) a balloon inflation port.

In another and/or alternative non-limiting aspect of the present disclosure, the delivery handle arrangement optionally includes a hypotube that is contained within the inner core or the housing. The hypotube is optionally configured to allow fluid (e.g., liquid, etc.) to flow over, about and/or through the balloon catheter and into the catheter. In one non-limiting embodiment, an O-ring is optionally provided so as to create a sliding hemostatic seal between an inner surface of the inner core and an outer surface of the hypotube. The hypotube can be configured to move linearly within the housing along the longitudinal axis of the housing.

In another and/or alternative non-limiting aspect of the present disclosure, the medical device that is used with the delivery handle arrangement is a prosthetic valve, a stent, inflatable balloon, or LAA (left atrial appendage) closure device.

In another and/or alternative non-limiting aspect of the present disclosure, there is provided a system that delivers an expandable medical device to a treatment site. The system includes a flexible catheter; a balloon catheter that is disposed coaxially with and moveable within the flexible catheter; and a delivery handle arrangement. In one non-limiting embodiment, the delivery handle arrangement includes a housing having an inner core that extends linearly between a proximal end and a distal end of the housing, and wherein the inner core receives at least a portion of the flexible catheter and the balloon catheter; and wherein an longitudinal adjustment mechanism is configured to control a position of the balloon catheter relative to the flexible catheter, and wherein the longitudinal adjustment mechanism includes a control knob that optionally has a plurality of threads; and a shaft (e.g., a threaded shaft, etc.) that is configured to translate linearly along a longitudinal axis of the housing within the housing; and wherein a switch is optionally configured to lock and/or unlocked the longitudinal adjustment mechanism, and wherein a) when the switch in the first position or locked position, the shaft can only be moved linearly from the proximal end towards the distal end within the housing when the control knob is rotated, and b) when the switch in the second position or unlocked position, the alignment knob of the rotational mechanism is configured to be pushed so as to advance the threaded shaft or hypotube towards the distal end and/or pulled so as to retreat the threaded shaft or hypotube towards the proximal end when the switch is in the second or unlocked position.

In another and/or alternative non-limiting aspect of the present disclosure, the delivery handle arrangement optionally includes a commissural alignment feature. One non-limiting arrangement of a commissural alignment feature can include a commissural alignment knob that can be used to rotate the catheter or balloon catheter to achieve proper alignment of the medical device at a treatment site (e.g., alignment of the commissural posts of the prosthetic valve to the commissures of the native aorta or other treatment sites when the medical device is a prosthetic valve, etc.). As can be appreciated, the commissural alignment feature can be used to obtain proper orientation of other types of medical devices at a treatment site. The commissural alignment feature on the delivery handle allows a user to rotate the balloon catheter and the prosthetic valve to achieve alignment of the commissural posts on the prosthetic valve to the commissures of the native aortic valve. In one non-limiting embodiment, the commissural alignment feature includes a commissural alignment knob that is rotatable connected to the housing. In another non-limiting embodiment, the luer tree of the delivery handle can optionally be configured be rotated by the user, and thereby optionally function as the commissural alignment knob. In such a non-limiting configuration the proximal end or end region of the shaft or hypotube can be connected to the luer tree such that the rotation of the luer tree results in rotation of the shaft or hypotube, which in turn causes rotation of the balloon catheter. In another non-limiting embodiment, the commissural alignment knob and/or the luer tree can be configured such that the commissural alignment knob and/or the luer tree can only be rotated when the longitudinal adjustment mechanism is in the unlocked position.

In another and/or alternative non-limiting aspect of the present disclosure, the delivery handle arrangement optionally includes various catheter features. Non-limiting catheter features can include one or more of a) a stylet that is configured to protect the guidewire lumen prior to use, b) a nose cone that is configured to provides a bonding site for the distal balloon bond, and/or to creates a rigid tapered leading edge for the balloon to cross the annulus, c) a balloon that is configured to be an expansion mechanism for the medical device, d) a guidewire lumen that is configured to form a lumen that spans the most or all of the catheter thereby allowing the medical device to be slid over a guide wire, and thereby guiding the medical device to the intended position at the treatment site (e.g., heart, etc.), e) one or more marker bands that are configured to be visual indicators to position the medical device on the balloon, f) an inflation spring that is configured to facilitate even expansion of the inflatable balloon during inflation of the inflatable balloon, g) a fluid passageway that is configured to form a pathway for saline and/or other liquids or fluids to enter the inflation balloon and cause expansion of the inflation balloon, h) a medical device support that is configured to provide support for the medical device (e.g., prosthetic valve, etc.) as it travels to the treatment site (e.g., aorta, etc.), i) a flexible catheter that is configured to house at least a portion of the balloon catheter, and wherein the flexible catheter can be configured to be flexed to maneuver a medical device around the aortic arch or other regions of the heart or other treatment areas.

In another and/or alternative non-limiting aspect of the present disclosure, the delivery handle arrangement in arrangement with the present disclosure includes: (i) a flex mechanism that is configured to facilitate in bending or flexing a distal region of the flexible catheter (e.g., flex or bend the distal region of the flexible catheter around various bends or arches [e.g. aortic arch bend], etc.) and to adjust alignment of the medical device at a treatment site (e.g., obtain coaxial alignment of the crimped prosthetic valve with the aortic annulus prior to expansion of the prosthetic valve, etc.); (ii) a longitudinal adjustment mechanism that is configured to advance or retract the balloon catheter's axial position relative to the flexible catheter; and (iii) a commissure alignment mechanism that is configured to rotate the balloon catheter so as to properly orient the medical device at a treatment site (e.g., rotate a crimped prosthetic valve and control the rotational orientation of the prosthetic valve leaflet attachment points (commissure) relative to the native anatomical valve of the heart prior to the expansion of the prosthetic valve at the treatment site, etc.). In one non-limiting arrangement, the adjustment mechanism can advantageously be transitioned using a switch between a locked position for fine longitudinal movement of the balloon catheter relative to the flexible catheter, and an unlocked position for larger longitudinal movement of the balloon catheter relative to the flexible catheter.

In another and/or alternative non-limiting aspect of the present disclosure, when the medical device is a prosthetic valve, the prosthetic valve is not limited to a TAV, but can be mitral valve replacement, tricuspid valve replacement, pulmonary or valve replacement. The prosthetic valve includes a radially collapsible and expandable frame and a leaflet structure comprising a plurality of leaflets. The prosthetic valve can optionally include an outer skirt disposed on at least a portion of an outer surface of the expandable frame and overlying a plurality of cells of at least a portion of the frame. The prosthetic valve can also or alternatively include an inner skirt. The expandable frame can optionally comprise a plurality of interconnected struts and strut joints defining a plurality of open cells in the expandable frame. As can be appreciated, the expandable frame can have other configurations. The expandable frame is optionally partially (e.g., 1-99.999 wt. % and all values and ranges therebetween) or fully made of a metal material.

In another and/or alternative non-limiting aspect of the present disclosure, the medical device is in the form of a prosthetic valve that includes a frame, a leaflet structure supported by the frame, and an optional inner skirt secured to the surface of the frame and/or leaflet structure, and an optional outer skirt that is secured to the frame. The prosthetic valve can be implanted in the annulus of the native aortic valve; however, the prosthetic valve also can be configured to be implanted in other valves of the heart (e.g., tricuspid valve, pulmonary valve, mitral valve). The prosthetic valve has a "lower" end and an "upper" end, wherein the lower end of the prosthetic valve is the inflow end and the upper end of the prosthetic valve is the outflow end. The metal alloy that is optionally used to partially or fully form the expandable frame of the prosthetic valve is configured to be radially collapsible to a collapsed or crimped state for introduction into the body (e.g., on a delivery catheter, balloon catheter, etc.) and radially expandable to an expanded state for implanting the prosthetic valve at a desired location in the body (e.g., the aortic valve, tricuspid valve, pulmonary valve, mitral valve, etc.). The expandable frame of the prosthetic valve can be formed of a plastically-expandable material that permits crimping of the expandable frame to a smaller profile for delivery and expansion of the expandable frame. The expansion of the crimped expandable frame of the prosthetic valve can be by an expansion device such as, but not limited to, a balloon of on a balloon catheter; however, the expandable frame can optionally be partially (e.g., 1-99.999 wt. % and all values and ranges therebetween) or fully formed of a self-expanding material (e.g., Nitinol, etc.). The expandable frame is optionally at least partially (e.g., 1-99.999 wt. % and all values and ranges therebetween) formed of a plurality of angularly spaced, vertically extending posts, or struts. The posts or struts can optionally be interconnected via a lower row of circumferentially extending struts and an upper row of circumferentially extending struts via strut joints. The struts can be arrangement in a variety of patterns (e.g., zig-zag pattern, saw-tooth pattern, triangular pattern, polygonal pattern, oval pattern, etc.). One or more of the posts and/or struts can have the same or different thicknesses and/or cross-sectional shape and/or cross-sectional area.

In another and/or alternative non-limiting aspect of the present disclosure, the inner skirt of the prosthetic valve can be formed of a variety of flexible materials (e.g., polymer [e.g., polyethylene terephthalate (PET), polyester, nylon, Kevlar,®, silicon, etc.], composite material, metal, fabric material, etc.). In one non-limiting embodiment, the material used to partially (e.g., 1-99.999 wt. % and all values and ranges therebetween) or fully form the inner skirt can optionally be substantially non-elastic (i.e., substantially non-stretchable and non-compressible). In another non-limiting embodiment, the material used to partially or fully form the inner skirt can optionally be a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The size, configuration, and thickness of the inner skirt is non-limiting (e.g., thickness of 0.1-20 mils and all values and ranges therebetween). The inner skirt can be secured to the inside and/or outside of the frame using various means (e.g., sutures, clamp arrangement, etc.). The inner skirt can be connected to one or more of the leaflets of the leaflet arrangement.

In another and/or alternative non-limiting aspect of the present disclosure, the outer skirt of the prosthetic valve can be used to 1) at least partially seal and/or prevent paravalvular leakage. The outer skirt can be positioned at least partially (e.g., 1-99.999 wt. % and all values and ranges therebetween) about the exterior region of the frame. The outer skirt or sleeve generally is positioned completely around a portion of the outside of the frame. Generally, the outer skirt is positioned about the lower portion of the frame, but does not fully cover the upper half of the frame; however, this is not required. The outer skirt can be connected to the frame by a variety of arrangements (e.g., sutures, adhesive, melted connection, clamping arrangement, etc.). At least a portion of the outer skirt can optionally be located on the interior surface of the frame. Generally, the outer skirt is formed of a more flexible and/or compressible material than the inner skirt; however, this is not required. The outer skirt can be formed of a variety of a stretchable and/or compressible material (e.g., silicone, PTFE, ePTFE, polyurethane, polyolefins, hydrogels, biological materials [e.g., pericardium or biological polymers such as collagen, gelatin, or hyaluronic acid derivatives], etc.). The outer skirt can optionally be formed from a combination of a cloth or fabric material that is coated with the stretchable and/or compressible material to provide additional structural integrity to the outer skirt. The size, configuration, and thickness of the outer skirt is non-limiting. The thickness of the outer skirt is generally 0.1-20 mils (and all values and ranges therebetween).

In another and/or alternative non-limiting aspect of the present disclosure, the prosthetic valve can include a leaflet structure that can be attached to the expandable frame and/or outer and/or inner skirts. The connection arrangement used to secure the leaflet structure to the expandable frame and/or inner and/or outer skirts is non-limiting (e.g., sutures, staples, melted bold, adhesive, clamp arrangement, etc.). The material used to form the leaflet structure can include bovine pericardial tissue, biocompatible synthetic materials, or various other suitable natural or synthetic materials. The leaflet structure generally comprises two or more leaflets (e.g., 2, 3, 4, 5, 6, etc.). In one non-limiting arrangement, the leaflet structure includes three leaflets arranged to collapse in a tricuspid arrangement. The configuration of the leaflet structures is non-limiting. The leaflets of the leaflet structure can optionally be secured to one another at their adjacent sides to form commissures of the leaflet structure (the edges where the leaflets come together). The leaflet structure can be secured together by a variety of connection arrangement (e.g., sutures, adhesive, melted bond, clamping arrangement, etc.). The leaflets can optionally include reinforcing structures or strips to 1) facilitate in securing the leaflets together, 2) facilitate in securing the leaflets to the skirt and/or frame, and/or 3) inhibit or prevent tearing or other types of damage to the leaflets.

In another and/or alternative non-limiting aspect of the present disclosure, the expandable frame of the medical device can be partially (e.g. 1-99.999 wt. % and all values and ranges therebetween) or fully formed of a metal alloy that includes a) stainless-steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, m) metal alloy (e.g., stainless-steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that is modified to further include at least 5 atomic weight percent (awt. %) or atomic percent (awt. %) rhenium (e.g., 5-99 awt. % rhenium and all values and ranges therebetween), or n) metal alloy (e.g., stainless-steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that is modified to further include at least 5 atomic weight percent (awt. %) or atomic percent (awt. %) hafnium (e.g., 5-99 awt. % hafnium and all values and ranges therebetween). As used herein, atomic weight percent (awt. %) or atomic percentage (awt %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. It has been found that for several metal alloys the inclusion of rhenium and/or hafnium results in the ductility and/or tensile strength of the metal alloy to improve as compared to a metal alloy is that absent rhenium and/or hafnium. Such improvement in ductility and/or tensile strength due to the inclusion of at least 5-15 awt. % rhenium and/or 5-15 awt. % hafnium in the metal alloy is referred to as the "rhenium effect" or "hafnium effect." As defined herein, a "rhenium effect" or a "hafnium effect" is a) an increase of at least 10% in ductility of the metal alloy caused by the addition of rhenium and/or hafnium to the metal alloy, and/or b) an increase of at least 10% in tensile strength of the metal alloy caused by the addition of rhenium and/or hafnium to the metal alloy. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. As used herein, atomic weight percent (awt. %) or atomic percentage (awt %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents.

In another and/or alternative non-limiting aspect of the present disclosure, the metal alloy used to partially or fully form the expandable frame of the medical device can include a) stainless steel, b) CoCr alloy, c) TiAlV alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, m) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 atomic weight percent (awt. %) or atomic percent (awt. %) rhenium (e.g., 5-99 awt. % rhenium and all values and ranges therebetween), or n) metal alloy (e.g., stainless steel, CoCr alloy, TiAlV alloy, aluminum alloy, nickel alloy, titanium alloy, tungsten alloy, molybdenum alloy, copper alloy, beryllium-copper alloy, titanium-nickel alloy, refractory metal alloy, etc.) that includes at least 5 atomic weight percent (awt. %) or atomic percent (awt. %) hafnium (e.g., 5-99 awt. % hafnium and all values and ranges therebetween). It has been found that for several metal alloys the inclusion of rhenium and/or hafnium results in the ductility and/or tensile strength of the metal alloy to improve as compared to a metal alloy is that absent rhenium and/or hafnium. Such improvement in ductility and/or tensile strength due to the inclusion of at least 5-15 awt. % rhenium and/or 5-15 awt. % hafnium in the metal alloy is referred to as the "rhenium effect" or "hafnium effect." As defined herein, a "rhenium effect" or a "hafnium effect" is a) an increase of at least 10% in ductility of the metal alloy caused by the addition of rhenium and/or hafnium to the metal alloy, and/or b) an increase of at least 10% in tensile strength of the metal alloy caused by the addition of rhenium and/or hafnium to the metal alloy.

In another and/or alternative non-limiting aspect of the present disclosure, the metal alloy used to partially or fully form the expandable frame of the medical device can include stainless-steel, CoCr alloys, TiAlV alloys, aluminum alloys, nickel alloys, titanium alloys, tungsten alloys, molybdenum alloys, copper alloys, MP35N alloys, or beryllium-copper alloys that have been modified to include at least 5-15 awt. % rhenium and/or 5-15 awt % hafnium so as to result in improved ductility and/or tensile strength as compared to the same metal alloy that is absent rhenium and/or hafnium. As defined herein, a stainless-steel alloy (SS alloy) includes at least 50 wt. % iron (e.g., 50-85 wt. % and all values and ranges therebetween), 10-30 wt. % chromium, 0-35 wt. % nickel, and optionally one or more of 0-5 wt. % molybdenum, 0-6 wt. % manganese, 0-1 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-72 wt. % cobalt, 15-35 wt. % chromium, and optionally one or more of 1-38 wt. % nickel, 2-18 wt. % molybdenum, 0-18 wt. % iron, 0-1 wt. % titanium, 0-2.8 wt. % manganese, 0-0.15 wt. % silver, 0-2 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox™ and Elgiloy™ alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. % yttrium. A Ti-6A1-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium. As defined herein, a stainless-steel alloy (SS alloy) includes at least 50 wt. % iron (e.g., 50-85 wt. % and all values and ranges therebetween), 10-30 wt. % chromium, 0-35 wt. % nickel, and optionally one or more of 0-5 wt. % molybdenum, 0-6 wt. % manganese, 0-1 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-72 wt. % cobalt, 15-35 wt. % chromium, and optionally one or more of 1-38 wt. % nickel, 2-18 wt. % molybdenum, 0-18 wt. % iron, 0-1 wt. % titanium, 0-2.8 wt. % manganese, 0-0.15 wt. % silver, 0-2 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox™ and Elgiloy™ alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. % yttrium. A Ti-6Al-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium. It will be appreciated that all component ranges of the alloys set forth in this application include the range, the end points of the range, and all values and ranges therebetween.

In another and/or alternative non-limiting aspect of the present disclosure, the metal alloy used to partially or fully form the expandable frame of the medical device can include at least 5 awt. % (e.g., 5-99 awt. % and all values and ranges therebetween) rhenium, and 0.1-96 wt. % (and all values and ranges therebetween) of one or more additives selected from the group of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.), and which metal alloy exhibits a rhenium effect. In one non-limiting embodiment, the metal alloy is a stainless-steel alloy that has been modified to include at least 5-15 awt. % rhenium. In another and/or alternative non-limiting embodiment, the metal alloy is a cobalt-chromium alloy that has been modified to include at least 5-15 awt. % rhenium. In another and/or alternative non-limiting embodiment, the metal alloy is a TiAlV alloy that has been modified to include at least 5-15 awt. % rhenium. In another and/or alternative non-limiting embodiment, the metal alloy is an aluminum alloy that has been modified to include at least 5-15 awt. % rhenium. In another and/or alternative non-limiting embodiment, the metal alloy is a nickel alloy that has been modified to include at least 5-15 awt. % rhenium. In another and/or alternative non-limiting embodiment, the metal alloy is a titanium alloy that has been modified to include at least 5-15 awt. % rhenium. In another and/or alternative non-limiting embodiment, the metal alloy is a tungsten alloy that has been modified to include at least 15 awt. % rhenium. In another and/or alternative non-limiting embodiment, the metal alloy is a molybdenum alloy that has been modified to include at least 5-15 awt. % rhenium. In another and/or alternative non-limiting embodiment, the metal alloy is a copper alloy that has been modified to include at least 5-15 awt. % rhenium. In another and/or alternative non-limiting embodiment, the metal alloy is a beryllium-copper alloy that has been modified to include at least 5-15 awt. % rhenium.

The metal alloy used to partially or fully form the expandable frame of the medical device can include at least 5 awt. % (e.g., 5-99 awt. % and all values and ranges therebetween) hafnium, and 0.1-96 wt. % (and all values and ranges therebetween) of one or more additives selected from the group of aluminum, boron, beryllium, bismuth, cadmium, calcium, cerium, chromium, cobalt, copper, gallium, gold, iridium, iron, lanthanum, lithium, magnesium, manganese, molybdenum, nickel, niobium, osmium, palladium, platinum, rare earth metals, rhenium, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.), and which metal alloy exhibits a hafnium effect. In one non-limiting embodiment, the metal alloy is a stainless-steel alloy that has been modified to include at least 5-15 awt. % hafnium. In another and/or alternative non-limiting embodiment, the metal alloy is a cobalt chromium alloy that has been modified to include at least 5-15 awt. % hafnium. In another and/or alternative non-limiting embodiment, the metal alloy is a TiAlV alloy that has been modified to include at least 5-15 awt. % hafnium. In another and/or alternative non-limiting embodiment, the metal alloy is an aluminum alloy that has been modified to include at least 5-15 awt. % hafnium. In another and/or alternative non-limiting embodiment, the metal alloy is a nickel alloy that has been modified to include at least 5-15 awt. % hafnium. In another and/or alternative non-limiting embodiment, the metal alloy is a titanium alloy that has been modified to include at least 5-15 awt. % hafnium. In another and/or alternative non-limiting embodiment, the metal alloy is a tungsten alloy that has been modified to include at least 5-15 awt. % hafnium. In another and/or alternative non-limiting embodiment, the metal alloy is a molybdenum alloy that has been modified to include at least 5-15 awt. % hafnium. In another and/or alternative non-limiting embodiment, the metal alloy is a copper alloy that has been modified to include at least 5-15 awt. % hafnium. In another and/or alternative non-limiting embodiment, the metal alloy is a beryllium-copper alloy that has been modified to include at least 5-15 awt. % hafnium.

In another and/or alternative non-limiting aspect of the present disclosure, the metal alloy used to partially or fully form the expandable frame of the medical device can include rhenium and/or hafnium, and molybdenum, and the weight percent of rhenium and/or hafnium in the metal alloy is optionally greater than the weight percent of molybdenum in the metal alloy, and the weight percent of one or more additive (e.g., aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium) in the metal alloy is optionally greater that the weight percent of molybdenum in the metal alloy, and the metal alloy optionally includes 0-2 wt. % of a combination of other components other than the additives (e.g., carbon, oxygen, phosphorous, sulfur, hydrogen, lead, nitrogen, etc.). In one non-limiting embodiment, the metal alloy is fully formed of or includes rhenium and/or hafnium, and molybdenum, and the weight percent of rhenium and/or hafnium plus the combined weight percent of additives is greater than the weight percent of molybdenum, and the metal alloy optionally includes 0-2 wt. % of a combination of other components other than the additives (e.g., carbon, oxygen, phosphorous, sulfur, hydrogen, lead, nitrogen, etc.).

In another and/or alternative non-limiting aspect of the present disclosure, the metal alloy used to partially or fully form the expandable frame of the medical device can include rhenium and/or hafnium, and molybdenum, and one or more additives selected from bismuth, niobium, tantalum, tungsten, titanium, vanadium, chromium, manganese, yttrium, zirconium, technetium, ruthenium, rhodium, hafnium, osmium, copper, and iridium, and the atomic weight percent of rhenium and/or hafnium to the atomic weight percent of the combination of one or more of bismuth, niobium, tantalum, tungsten, titanium, vanadium, chromium, manganese, yttrium, zirconium, technetium, ruthenium, rhodium, hafnium, osmium, copper, and iridium is 0.4:1 to 2.5:1 (and all values and ranges therebetween).

In another and/or alternative non-limiting aspect of the present disclosure, the metal alloy used to partially or fully form the expandable frame of the medical device can include at least 5 awt. % (e.g., 5-99 awt. % and all values and ranges therebetween) rhenium and/or hafnium plus at least two metals selected from the group of molybdenum, bismuth, chromium, iridium, niobium, tantalum, titanium, yttrium, and zirconium, and the content of the metal alloy that includes other elements and compounds is 0-0.1 wt. %. In another and/or alternative non-limiting embodiment, the metal alloy includes rhenium and/or hafnium, molybdenum, and chromium. In another and/or alternative non-limiting embodiment, the metal alloy includes at least 35 wt. % (e.g., 35-75 wt. % and all values and ranges therebetween) rhenium and/or hafnium, and the metal alloy also includes chromium. In one non-limiting embodiment, the metal alloy includes at least 35 wt. % rhenium and/or hafnium, and at least 25 wt. % (e.g., 25-49.9 wt. % and all values and ranges therebetween) of the metal alloy includes chromium, and optionally 0.1-40 wt. % (and all values and ranges therebetween) of the metal alloy includes one or more of aluminum, boron, beryllium, bismuth, cadmium, calcium, cerium, chromium, cobalt, copper, gallium, gold, hafnium, iridium, iron, lanthanum, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other metals, carbon, oxygen, phosphorous, sulfur, hydrogen and/or nitrogen. In another and/or alternative non-limiting embodiment, the metal alloy includes 15-50 awt. % rhenium and/or hafnium (and all values and ranges therebetween) and 0.5-70 awt. % chromium (and all values and ranges therebetween). In another and/or alternative non-limiting embodiment, the metal alloy includes 15-50 awt. % rhenium and/or hafnium (and all values and ranges therebetween) and 0.5-70 awt. % tantalum (and all values and ranges therebetween). In another and/or alternative non-limiting embodiment, the metal alloy includes 15-50 awt. % rhenium and/or hafnium (and all values and ranges therebetween) and 0.5-70 awt. % niobium (and all values and ranges therebetween). In another and/or alternative non-limiting embodiment, the metal alloy includes 15-50 awt. % rhenium and/or hafnium (and all values and ranges therebetween) and 0.5-70 awt. % titanium (and all values and ranges therebetween). In another and/or alternative non-limiting embodiment, the metal alloy includes 15-50 awt. % rhenium and/or hafnium (and all values and ranges therebetween) and 0.5-70 awt. % zirconium (and all values and ranges therebetween). In another and/or alternative non-limiting embodiment, the metal alloy includes 15-50 awt. % rhenium and/or hafnium (and all values and ranges therebetween) and 0.5-70 awt. % molybdenum (and all values and ranges therebetween). In another and/or alternative non-limiting embodiment, the metal alloy includes at least 15 awt. % rhenium and/or hafnium, greater than 50 wt. % titanium (e.g., 51-80 wt. % and all values and ranges therebetween), 15-45 wt. % (and all values and ranges therebetween) niobium, 0-10 wt. % (and all values and ranges therebetween) zirconium, 0-15 wt. % (and all values and ranges therebetween) tantalum, and 0-8 wt. % molybdenum (and all values and ranges therebetween).

In another and/or alternative non-limiting aspect of the present disclosure, the metal alloy used to partially or fully form the expandable frame of the medical device can include a refractory metal alloy, and wherein the refractory metal alloy includes at least 20 wt. % of one or more of niobium, rhenium, tantalum, molybdenum or tungsten (e.g., 20-99.9 wt. % and all values and ranges therebetween), and 0.1-80 wt. % (and all values and ranges therebetween) of one or more of calcium, carbon, cerium oxide, chromium, cobalt, copper, gold, hafnium, iridium, iron, lanthanum, lanthanum oxide, magnesium, manganese, molybdenum, nickel, osmium, platinum, rare earth metals, rhodium, ruthenium, silver, tantalum, technetium, titanium, vanadium, yttrium, yttrium oxide, zinc, zirconium, zirconium oxide, and/or alloys of one or more of such components.

In another and/or alternative non-limiting aspect of the present disclosure, the metal alloy used to partially or fully form the expandable frame of the medical device can include a refractory metal alloy, and wherein the refractory metal alloy includes at least 5 awt. % rhenium and/or hafnium, at least 20 wt. % of one or more of niobium, tantalum, molybdenum or tungsten (e.g., 20-99.9 wt. % and all values and ranges therebetween), and 0-80 wt. % (and all values and ranges therebetween) of one or more of calcium, carbon, cerium oxide, chromium, cobalt, copper, gold, hafnium, iridium, iron, lanthanum, lanthanum oxide, magnesium, manganese, molybdenum, nickel, osmium, platinum, rare earth metals, rhodium, ruthenium, silver, tantalum, technetium, titanium, vanadium, yttrium, yttrium oxide, zinc, zirconium, zirconium oxide, and/or alloys of one or more of such components.

In another and/or alternative non-limiting aspect of the present disclosure, the metal alloy used to partially or fully form the expandable frame of the medical device can include a refractory metal alloy, and wherein the refractory metal alloy includes at least 20 wt. % of one or more of niobium, tantalum or tungsten, and wherein the refractory metal alloy includes 0-30 wt. % molybdenum (and all values and ranges therebetween), and wherein the refractory metal alloy includes at least 5 awt. % rhenium and/or hafnium (e.g., 5-80 awt. % rhenium and/or hafnium and all values and ranges therebetween), and wherein the refractory metal alloy includes and 0-80 wt. % (and all values and ranges therebetween) of one or more of calcium, carbon, cerium oxide, chromium, cobalt, copper, gold, hafnium, iridium, iron, lanthanum, lanthanum oxide, magnesium, manganese, molybdenum, nickel, osmium, platinum, rare earth metals, rhodium, ruthenium, silver, tantalum, technetium, titanium, vanadium, yttrium, yttrium oxide, zinc, zirconium, zirconium oxide, and/or alloys of one or more of such components.

In another and/or alternative non-limiting aspect of the present disclosure, the metal alloy used to partially or fully form the expandable frame of the medical device can include at least 5 awt. % rhenium and/or hafnium (e.g., 5-99 awt. % rhenium and/or hafnium and all values and ranges therebetween), and at least 0.1 wt. % of one or more additive metals selected from aluminum, bismuth, chromium, cobalt, copper, hafnium, iridium, iron, magnesium, manganese, nickel, niobium, osmium, rhodium, ruthenium, silicon, silver, tantalum, technetium, titanium, tungsten, vanadium, yttrium, and zirconium, and wherein the metal alloy includes 0-30 wt. % molybdenum (and all values and ranges therebetween), and wherein a combined weight percent of rhenium and/or hafnium, and the additive metals is 70-100 wt. % (and all values and ranges therebetween).

In another and/or alternative non-limiting aspect of the present disclosure, the metal alloy used to partially or fully form the expandable frame of the medical device can include stainless-steel that has been modified with at least 5 awt. % rhenium and/or hafnium (e.g., 5-50 awt. % rhenium and/or hafnium and all values and ranges therebetween), and wherein a combined weight percent of iron, chromium, nickel, tantalum, niobium, copper, manganese, aluminum, titanium, selenium, vanadium, tungsten, hafnium and rhenium is 70-100 wt. % (and all values and ranges therebetween).

In another and/or alternative non-limiting aspect of the present disclosure, the metal alloy used to partially or fully form the expandable frame of the medical device can include cobalt-chromium alloy that has been modified with at least 5 awt. % rhenium and/or hafnium (e.g., 5-50 awt. % rhenium and/or hafnium and all values and ranges therebetween), and wherein a combined weight percent of cobalt, chromium, nickel, iron, titanium, manganese, silver, tungsten, silicon, aluminum, iron, boron, silver, titanium, hafnium, and rhenium is 70-100 wt. % (and all values and ranges therebetween).

In another and/or alternative non-limiting aspect of the present disclosure, the metal alloy used to partially or fully form the expandable frame of the medical device can include titanium-aluminum-vanadium alloy that has been modified with at least 5 awt. % rhenium and/or hafnium (e.g., 5-50 awt. % rhenium and/or hafnium and all values and ranges therebetween), and wherein a combined weight percent of aluminum, vanadium, titanium, iron, yttrium, hafnium, and rhenium is 70-100 wt. % (and all values and ranges therebetween).

In another and/or alternative non-limiting aspect of the present disclosure, the metal alloy used to partially or fully form the expandable frame of the medical device can include aluminum alloy that has been modified with at least 5 awt. % rhenium and/or hafnium (e.g., 5-50 awt. % rhenium and/or hafnium and all values and ranges therebetween), and wherein a combined weight percent of aluminum, silicon, magnesium, manganese, scandium, beryllium, yttrium, cerium, chromium, iron, zinc, titanium, lithium, silver, calcium, zirconium, cadmium, bismuth, nickel, vanadium, gallium, copper, hafnium, and rhenium is 70-100 wt. % (and all values and ranges therebetween).

In another and/or alternative non-limiting aspect of the present disclosure, the metal alloy used to partially or fully form the expandable frame of the medical device can include nickel alloy that has been modified with at least 5 awt. % rhenium and/or hafnium (e.g., 5-50 awt. % rhenium and/or hafnium and all values and ranges therebetween), and wherein a combined weight percent of nickel, chromium, iron, copper, cobalt, aluminum, tantalum, tungsten, titanium, niobium, silicon, hafnium, and rhenium is 70-100 wt. % (and all values and ranges therebetween).

In another and/or alternative non-limiting aspect of the present disclosure, the metal alloy used to partially or fully form the expandable frame of the medical device can include titanium alloy that has been modified with at least 5 awt. % rhenium and/or hafnium (e.g., 5-50 awt. % rhenium and/or hafnium and all values and ranges therebetween), and wherein a combined weight percent of titanium, aluminum, tin, palladium, vanadium, nickel, ruthenium, chromium, zirconium, niobium, silicon, cobalt, iron, hafnium, and rhenium is 70-100 wt. % (and all values and ranges therebetween).

In another and/or alternative non-limiting aspect of the present disclosure, the metal alloy used to partially or fully form the expandable frame of the medical device can include tungsten alloy that has been modified with at least 5 awt. % rhenium and/or hafnium (e.g., 5-50 awt. % rhenium and/or hafnium and all values and ranges therebetween), and wherein a combined weight percent of tungsten, nickel, copper, iron, hafnium, and rhenium is 70-100 wt. % (and all values and ranges therebetween).

In another and/or alternative non-limiting aspect of the present disclosure, the metal alloy used to partially or fully form the expandable frame of the medical device can include copper alloy that has been modified with at least 5 awt. % rhenium and/or hafnium (e.g., 5-50 awt. % rhenium and/or hafnium and all values and ranges therebetween), and wherein a combined weight percent of copper, zinc, tin, iron, silicon, manganese, aluminum, beryllium, cobalt, nickel, hafnium, and rhenium is 70-100 wt. % (and all values and ranges therebetween). In another and/or alternative non-limiting aspect of the present disclosure.

In another and/or alternative non-limiting aspect of the present disclosure, the metal alloy used to partially or fully form the expandable frame of the medical device can include beryllium-copper alloy that has been modified with at least 5 awt. % rhenium and/or hafnium (e.g., 5-50 awt. % rhenium and/or hafnium and all values and ranges therebetween), and wherein a combined weight percent of copper, beryllium, cobalt, silicon, hafnium, and rhenium is 70-100 wt. % (and all values and ranges therebetween).

In another and/or alternative non-limiting aspect of the present disclosure, the metal alloy used to partially or fully form the expandable frame of the medical device can include titanium-nickel alloy that has been modified with at least 5 awt. % rhenium and/or hafnium (e.g., 5-50 awt. % rhenium and/or hafnium and all values and ranges therebetween), and wherein a combined weight percent of nickel, titanium, hafnium, and rhenium is 70-100 wt. % (and all values and ranges therebetween).

In another and/or alternative non-limiting aspect of the present disclosure, the metal alloy used to partially or fully form the expandable frame of the medical device can includes a primary metal (5-95 wt. % primary metal and all values and ranges therebetween) selected from one or more of molybdenum, rhenium, hafnium, niobium, tantalum, tungsten, and one or more alloying agents such as, but are not limited to, calcium, carbon, cerium oxide, chromium, cobalt, copper, gold, hafnium, iron, lanthanum oxide, magnesium, nickel, osmium, platinum, rare earth metals, rhenium, silver, technetium, titanium, vanadium, yttrium, yttrium oxide, zinc, zirconium, zirconium oxide, and/or alloys of one or more of such components (e.g., MoHfC, $MoY_2O_3$, $MoCs_2O$, MoW, MoTa, $MoZrO_2$, $MoLa_2O_3$, MoRe alloy, MoReW alloy, HfMo alloy, HfW alloy, ReW alloy, etc.), and wherein metal alloy optionally includes less than about 5 wt. % (e.g., 0-4.999999 wt. % and all values and ranges therebetween) of a combination a) metals of than the primary metal, b) metals or compounds other the alloying agents, c) oxygen, d) nitrogen, and e) other metals and/or impurities.

In another and/or alternative non-limiting aspect of the present disclosure, the metal alloy used to partially or fully form the expandable frame of the medical device can include tungsten and copper and optionally one or more metal agents such as, but are not limited to, calcium, carbon, cerium oxide, chromium, cobalt, gold, hafnium, iron, lanthanum oxide, magnesium, molybdenum, nickel, niobium, osmium, platinum, rare earth metals, rhenium, silver, tantalum, technetium, titanium, vanadium, yttrium, yttrium oxide, zinc, zirconium, zirconium oxide, and/or alloys of one or more of such components. In one non-limiting formulation, the metal alloy includes 1-99.9 wt. % tungsten (and all values and ranges therebetween) (e.g., 1 wt. %, 1.01 wt. %, 1.02 wt. % . . . 99.88 wt. %, 99.89 wt. %, 99.9 wt. %), and 0.1-99 wt. % copper (and all values and ranges therebetween) (e.g., 0.1 wt. %, 0.101 wt. %, 0.102 wt. % . . . 98.998 wt. %, 98.999 wt. %, 99 wt. %). In another non-limiting formulation, the tungsten constitutes the greatest weight percent in the metal alloy and the copper constitutes the second greatest weight percent in the metal alloy. In another non-limiting formulation, the tungsten constitutes the largest weight percent of any component that forms the metal alloy. In another non-limiting formulation, the tungsten constitutes greater than 50 wt. % of the metal alloy.

In another and/or alternative non-limiting aspect of the present disclosure, the metal alloy used to partially or fully form the expandable frame of the medical device can include tungsten and rhenium and/or hafnium, and optionally one or more alloying agents such as, but not limited to, calcium, carbon, cerium oxide, chromium, cobalt, copper, gold, hafnium, iron, lanthanum oxide, magnesium, molybdenum, nickel, niobium, osmium, platinum, rare earth metals, rhenium, silver, tantalum, technetium, titanium, tungsten, vanadium, yttrium, yttrium oxide, zinc, zirconium, zirconium oxide, and/or alloys of one or more of such components (e.g., WRe, WReMo, WHf, WHfMo, WHfRe, WHfReMo, etc.). In one non-limiting formulation, the metal alloy includes 1-40 wt. % rhenium and/or hafnium (and all values and ranges therebetween and 60-99 wt. % tungsten (and all values and ranges therebetween). The total weight percent of the tungsten, rhenium and hafnium in the metal alloy is at least about 95 wt. % (e.g., 95-100% and all values and ranges therebetween). In another non-limiting formulation, the metal alloy includes 1-47.5 wt. % rhenium and/or hafnium (and all values and ranges therebetween) and 20-80 wt. % tungsten (and all values and ranges therebetween) and 0-47.5 wt. % molybdenum (and all values and ranges therebetween). The total weight percent of the tungsten, molybdenum, rhenium and hafnium in the metal alloy is at least about 95 wt. % (e.g., 95-100% and all values and ranges therebetween). In one non-limiting specific metal alloy, the weight percent of the tungsten is greater than a weight percent of rhenium, hafnium and/or molybdenum. In another non-limiting specific metal alloy, the weight percent of the tungsten is greater than 50 wt. % of the metal alloy. In another non-limiting specific metal alloy, the weight percent of the tungsten is greater than a weight percent of rhenium and/or hafnium, but is less than a weigh percent of molybdenum. In another non-limiting specific metal alloy, the weight percent of the tungsten is greater than a weight percent of molybdenum, but less than a weigh percent of rhenium and/or hafnium. In another non-limiting metal alloy, the weight percent of the tungsten is less than a weight percent of rhenium, hafnium and/or molybdenum.

In another and/or alternative non-limiting aspect of the present disclosure, the metal alloy used to partially or fully form the expandable frame of the medical device can include a metal alloy that has an atomic weight percent of rhenium and/or hafnium to the atomic weight percent of the combination of bismuth, niobium, tantalum, tungsten, titanium, vanadium, chromium, manganese, yttrium, zirconium, technetium, ruthenium, rhodium, hafnium, osmium, copper, and iridium in the metal alloy is 0.7:1 to 1.5:1 (and all values and ranges therebetween).

In another and/or alternative non-limiting aspect of the present disclosure, the metal alloy used to partially or fully form the expandable frame of the medical device can include two of bismuth, niobium, tantalum, tungsten, titanium, vanadium, chromium, manganese, yttrium, zirconium, technetium, ruthenium, rhodium osmium, copper, and iridium, the atomic ratio of the two metals is 0.4:1 to 2.5:1 (and all values and ranges therebetween).

In another and/or alternative non-limiting aspect of the present disclosure, the metal alloy used to partially or fully form the expandable frame of the medical device can include a titanium-nickel alloy that has been modified with at least 5 awt. % rhenium and/or hafnium (e.g., 5-50 awt. % rhenium and/or hafnium and all values and ranges therebetween), and wherein a combined weight percent of nickel, titanium, hafnium, and rhenium is 70-100 wt. % (and all values and ranges therebetween).

In another and/or alternative non-limiting aspect of the present disclosure, the metal alloy used to partially or fully form the expandable frame of the medical device can include at least 15 atw. % hafnium and/or rhenium and also includes one or more of molybdenum, niobium, tantalum, or tungsten.

In another and/or alternative non-limiting aspect of the present disclosure, the metal alloy used to partially or fully form the expandable frame of the medical device can include at least 15 atw. % hafnium and/or rhenium and 0.1-75 wt. % (and all values and ranges therebetween) of one or more of aluminum, bismuth, calcium, carbon, chromium, cobalt, copper, gold, iridium, iron, lanthanum, magnesium, manganese, molybdenum, nickel, niobium, osmium, platinum, rare earth metals, rhodium, ruthenium, silver, tantalum, technetium, titanium, tungsten, vanadium, yttrium, zinc, zirconium, and/or alloys of one or more of such components.

In another and/or alternative aspect of the present disclosure, the metal alloy used to partially or fully form the expandable frame of the medical device includes at least 15 atw. % hafnium and/or rhenium, nickel and tungsten and optionally one or more alloying agents such as, but not limited to, aluminum, bismuth, calcium, carbon, chromium, cobalt, copper, gold, iron, magnesium, molybdenum, niobium, osmium, platinum, rare earth metals, rhenium, silver, tantalum, technetium, titanium, vanadium, yttrium, zinc, zirconium, and/or alloys of one or more of such components (e.g., WNi, WNiMo, WNi.Re, etc.). In another non-limiting formulation, the metal alloy that includes at least 15 atw. % hafnium and/or rhenium includes 1-47.5 wt. % nickel (and all values and ranges therebetween) and 20-80 wt. % tungsten (and all values and ranges therebetween) and 1-47.5 wt. % (and all values and ranges therebetween) of one or more of aluminum, bismuth, calcium, carbon, chromium, cobalt, copper, gold, hafnium, iron, magnesium, molybdenum, nickel, niobium, osmium, platinum, rare earth metals, silver, tantalum, technetium, titanium, vanadium, yttrium, zinc, zirconium.

In another and/or alternative non-limiting aspect of the present disclosure, the metal alloy used to partially or fully form the expandable frame of the medical device can include at least 15 atw. % hafnium and/or rhenium and nickel.

In another and/or alternative non-limiting aspect of the present disclosure, the metal alloy used to partially or fully form the expandable frame of the medical device can include at least 15 atw. % hafnium and/or rhenium includes (e.g., 15-99 awt. % and all values and ranges therebetween), optionally 5 awt. % (e.g., 5-99 awt. % and all values and ranges therebetween) molybdenum, optionally 5 awt. % (e.g., 5-99 awt. % and all values and ranges therebetween) niobium, optionally 5 awt. % (e.g., 5-99 awt. % and all values and ranges therebetween) tantalum, optionally 5 awt. % (e.g., 5-99 awt. % and all values and ranges therebetween) tungsten, and at least 0.1 wt. % (e.g., 0.1 wt. % to 96 wt. % and all values and ranges therebetween) of one or more of aluminum, boron, beryllium, bismuth, cadmium, calcium, cerium, chromium, cobalt, copper, gallium, gold, iridium, iron, lanthanum, lithium, magnesium, manganese, nickel, osmium, palladium, platinum, rare earth metals, rhodium, ruthenium, scandium, silver, silicon, technetium, tin, titanium, vanadium, yttrium, zinc, and/or zirconium, and the metal alloy optionally includes 0-2 wt. % (and all values and ranges therebetween) of a combination of other metals, carbon, oxygen, phosphorous, sulfur, hydrogen and/or nitrogen.

In another and/or alternative non-limiting aspect of the present disclosure, the expandable frame can be formed of at least 30 wt. % (e.g., 30-100 wt. % and all values and ranges therebetween) of the metal alloy.

In another and/or alternative non-limiting aspect of the present disclosure, the metal alloy used to partially or fully form the expandable frame of the medical device can include less than 5 wt. % nickel (e.g., 0-4.99 wt. % and all values and ranges therebetween).

In another and/or alternative non-limiting aspect of the present disclosure, the metal alloy used to partially or fully form the expandable frame of the medical device can include less than 5 wt. % chromium (e.g., 0-4.99 wt. % and all values and ranges therebetween).

In another and/or alternative non-limiting aspect of the present disclosure, the metal alloy used to partially or fully form the expandable frame of the medical device is optionally subjected to one or more manufacturing processes. These manufacturing processes can include, but are not limited to, expansion, laser cutting, etching, crimping, annealing, drawing, pilgering, electroplating, electro-polishing, machining, plasma coating, 3D printing, 3D printed coatings, chemical vapor deposition, chemical polishing, swaging, cleaning, pickling, ion beam deposition or implantation, sputter coating, vacuum deposition, nitriding, laser cutting, EDM cutting, gun-drilling, compression, sintering, compression process, consolidation process, etc.

In another and/or alternative non-limiting aspect of the present disclosure, the metal alloy used to partially or fully form the expandable frame of the medical device optionally has a generally uniform density throughout the metal alloy, and also results in the desired yield and ultimate tensile strengths of the metal alloy. In one non-limiting embodiment, the density of the metal alloy that includes at least 15 atw. % rhenium and/or hafnium and/or is a refractory metal alloy is generally at least about 5 μm/cc (e.g., 5 μm/cc-21 μm/cc and all values and ranges therebetween; 10-20 μm/cc; etc.), and typically at least about 11-19 μm/cc.

In another and/or alternative non-limiting aspect of the present disclosure, the metal alloy used to partially or fully form the expandable frame of the medical device optionally includes a certain amount of carbon and oxygen; however, this is not required. The carbon to oxygen atomic ratio can be as low as about 0.2:1 (e.g., 0.2:1 to 50:1 and all values and ranges therebetween).

In another and/or alternative non-limiting aspect of the present disclosure, the metal alloy optionally includes a controlled amount of nitrogen; however, this is not required. In one non-limiting formulation, the metal alloy includes less than about 0.001 wt. % nitrogen (e.g., 0 wt. % to 0.0009999 wt. % and all values and ranges therebetween). In one non-limiting formulation of the metal alloy, the atomic ratio of carbon to nitrogen ion the metal alloy is at least about 1.5:1 (e.g., 1.5:1 to 400:1 and all values and ranges therebetween). In another non-limiting formulation of the metal alloy, the atomic ratio of oxygen to nitrogen is at least about 1.2:1 (e.g., 1.2:1 to 150:1 and all value and ranges therebetween).

In another and/or alternative non-limiting aspect of the present disclosure, the metal alloy used to partially or fully form the expandable frame of the medical device optionally is at least partially or fully formed from a tube or rod of metal alloy, or is formed into a shape that is at least 80% of the final net shape of the medical device (e.g., formed by 3D printing, formed by compression and/or sintering of metal alloy powder, formed by gun-drilling and/or EDM cutting, formed by swaging, etc.). When the metal alloy is formed into a rod, the rod can optionally be gun-drilled and/or subjected to EDM cutting or otherwise cut to form a tube from the rod.

In another and/or alternative non-limiting aspect of the present disclosure, the metal alloy used to partially or fully form the expandable frame of the medical device optionally can be at least partially or fully formed from by 3D printing. As can be appreciated, other portions of the medical device or other type of device can be formed by 3D printing.

In another and/or alternative non-limiting aspect of the present disclosure, the metal alloy used to partially or fully form the expandable frame of the medical device is optionally subjected to a swaging process; however, this is not required.

In another and/or alternative non-limiting aspect of the present disclosure, the metal alloy used to partially or fully form the expandable frame of the medical device can optionally be nitrided; however, this is not required.

In another and/or alternative non-limiting aspect of the present disclosure, the metal alloy used to partially or fully form the expandable frame of the medical device, just prior to or after being partially or fully formed into the desired medical device or other type of device, can optionally be cleaned, polished, sterilized, nitrided, etc., for final processing of the metal alloy.

In another and/or alternative non-limiting aspect of the present disclosure, the metal alloy or medical device can include, contain and/or be coated with one or more agents that facilitate in the success of the medical device and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungus and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The one or more agents can be coated on and/or impregnated in medical device by a variety of mechanisms such as, but not limited to, spraying (e.g., atomizing spray techniques, etc.), powder deposition, dip coating, flow coating, dip-spin coating, roll coating (direct and reverse), sonication, brushing, plasma deposition, depositing by vapor deposition, MEMS technology, and rotating mold deposition.

In another and/or alternative non-limiting aspect of the present disclosure, the one or more agents on and/or in the metal alloy or medical device, when used on the medical device, can be released in a controlled manner so the area in question to be treated is provided with the desired dosage of agent over a sustained period of time. One or more polymers can be used to at least partially control the release of one or more agents from the metal alloy or medical device can be porous or non-porous. The one or more agents can be inserted into and/or applied to one or more surface structures and/or micro-structures on the metal alloy or medical device, and/or be used to at least partially form one or more surface structures and/or micro-structures on the metal alloy or medical device.

In another and/or alternative non-limiting aspect of the present disclosure, the medical device can optionally include a marker material that facilitates enabling the medical device to be properly positioned in a body passageway (e.g., blood vessel, heart valve, etc.). The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). In one non-limiting embodiment, the marker material is visible to x-rays (i.e., radiopaque).

In another and/or alternative non-limiting aspect of the present disclosure, one or more components of the prosthetic valve (e.g., frame, inner skirt, outer skirt, leaflets, material used to secure leaflets to frame, etc.) can be partially (e.g., 1% to 99.99% and all values and ranges therebetween) or fully be coated with an enhancement coating to improve one or more properties of the prosthetic heat valve (e.g., change exterior color of material having coated surface, increase surface hardness by use of the coated surface, increase surface toughness material having coated surface, reduced friction via use of the coated surface, improve scratch resistance of material that has the coated surface, improve impact wear of coated surface, improve resistance to corrosion and oxidation of coated material, form a non-stick coated surface, improve biocompatibility of material having the coated surface, reduce toxicity of material having the coated surface, reduce ion release from material having the coated surface, the enhancement coating forms a surface that is less of an irritant to cell about the coated surface after the prosthetic valve is implanted, reduces the rate to which cells grown on coated surface after prosthetic valve is implanted, reduce rate to which leaflets fail to properly operate after prosthetic valve is implanted, promote production and/or release of NO, etc.). In one non-limiting embodiment, only the expandable frame of the prosthetic valve includes the enhancement coating, and wherein the frame is partially (e.g., 1-99.99% and all values and ranges therebetween) or fully coated with the enhancement coating. In another non-limiting embodiment, only one or more of all of the leaflets of the prosthetic valve include the enhancement coating, and wherein one or more or all of the leaflets are partially (e.g., 1-99.99% and all values and ranges therebetween) or fully coated with the enhancement coating. In another non-limiting embodiment, only the inner skirt of the prosthetic valve includes the enhancement coating, and wherein the inner skirt is partially (e.g., 1-99.99% and all values and ranges therebetween) or fully coated with the enhancement coating. In another non-limiting embodiment, only the outer skirt of the prosthetic valve includes the enhancement coating, and wherein the outer skirt is partially (e.g., 1-99.99% and all values and ranges therebetween) or fully coated with the enhancement coating. In another non-limiting embodiment, two or more or all of a) the expandable frame, b) one or more or all of the leaflets, c) the inner skirt and d) the outer skirt of the prosthetic valve are partially (e.g., 1-99.99% and all values and ranges therebetween) or are fully coated with the enhancement coating. Non-limiting enhancement coatings that can be applied to a portion or all of the outer surface of one or more components of the prosthetic valve includes chromium nitride (CrN), diamond-like carbon (DLC), titanium nitride (TiN), titanium oxynitride or titanium nitride oxide ($TiNO_x$), zirconium nitride (ZrN), zirconium oxide ($ZrO_2$), zirconium oxynitride ($ZnN_xO_y$) [e.g., cubic ZrN:O, cubic $ZrO_2$:N, tetragonal $ZrO_2$:N, and monoclinic $ZrO_2$:N phase coatings], oxyzirconium-nitrogen-carbon (ZrNC), zirconium OxyCarbide (ZrOC), and combinations of such coatings. In one non-limiting embodiment, the one or more enhancement coatings are optionally applied to a portion or all of the outer surface of one or more components of the prosthetic valve by a vacuum process using an energy source to vaporize material and deposit a thin layer of enhancement coating material. Such vacuum coating process, when used, can include a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In another non-limiting embodiment, the thickness of the enhancement coating is greater than 1 nanometer (e.g., 2 nanometers to 100 microns and all values and ranges therebetween), and typically 0.1-25 microns, and more typically 0.2-10 microns. As defined herein, the enhancement coating does not include and is different from the optional agent coating or the optional nitriding coating.

One non-limiting object of the present disclosure is the provision of a delivery handle arrangement that facilitates the delivery of a medical device to a treatment site.

In another and/or alternative non-limiting object of the present disclosure is the provision of a delivery handle arrangement that includes a) a housing that has an inner core that extends linearly between a proximal end and a distal end of the housing, and wherein the inner core at least partially receives a flexible catheter and a balloon catheter, and wherein the flexible catheter and the balloon catheter are at least partially disposed coaxially within the housing; b) an longitudinal adjustment mechanism that is configured to control a position of the balloon catheter relative to the flexible catheter, and wherein the longitudinal adjustment mechanism includes a control knob that has a connection arrangement (e.g., a plurality of threads, etc.), a shaft (e.g., a threaded shaft, etc.) that is configured to translate linearly within the housing, and a switch that is configured to lock or unlocked the longitudinal adjustment mechanism.

In another and/or alternative non-limiting object of the present disclosure is the provision of a delivery handle arrangement that optionally includes a flex mechanism that is configured to controllably flex or bend the distal region of the flexible catheter.

In another and/or alternative non-limiting object of the present disclosure is the provision of a delivery handle arrangement that optionally includes a flex mechanism that includes a) a flex knob coupled to a body (e.g., a threaded body, etc.), wherein the body is at least partially contained within the housing, b) an insert (e.g., a threaded insert, etc.) that is engaged with the body, c) an actuation insert having a crimp band, and d) a wire member coupled to the distal region of the flexible catheter and the crimp band.

In another and/or alternative non-limiting object of the present disclosure is the provision of a delivery handle arrangement that optionally includes a flex indicator (e.g., a needle and/or other visual indicator (e.g., meter, digital readout, etc.)) that is used to indicate the amount and/or a degree of bend or flex present in the distal region of the flexible catheter.

In another and/or alternative non-limiting object of the present disclosure is the provision of a delivery handle arrangement that optionally includes a rotational mechanism that is configured to at least partially rotate the balloon catheter relative to the flexible catheter.

In another and/or alternative non-limiting object of the present disclosure is the provision of a delivery handle arrangement that optionally includes a rotational mechanism that is configured to at least partially rotate the balloon catheter relative to the flexible catheter, and wherein the rotational mechanism includes a) an alignment knob that is coupled to a shaft (e.g., a threaded shaft, etc.) of the adjustment mechanism, and b) a gear, and wherein rotation of the alignment knob causes the balloon catheter to rotate relative to the flexible catheter.

In another and/or alternative non-limiting object of the present disclosure is the provision of a delivery handle arrangement that optionally includes a longitudinal adjustment mechanism that is configured to cause linear adjustment of the shaft in the housing, which shaft is connected to the flexible catheter and/or balloon catheter.

In another and/or alternative non-limiting object of the present disclosure is the provision of a delivery handle arrangement that optionally includes a longitudinal adjustment mechanism that is configured to cause linear adjustment of the shaft or hypotube, and wherein the longitudinal adjustment mechanism includes a control knob and a switch, and wherein the switch is configured lock and unlock the longitudinal adjustment mechanism.

In another and/or alternative non-limiting object of the present disclosure is the provision of a delivery handle arrangement that optionally includes a rotational mechanism that is configured to at least partially cause rotation of the balloon catheter relative to the flexible catheter, and wherein an alignment knob of the rotational mechanism is configured to be pushed to advance the hypotube or shaft (e.g., the threaded shaft, etc.) towards the distal end, and wherein the alignment knob is configured to be pulled to retreat the shaft towards the proximal end.

In another and/or alternative non-limiting object of the present disclosure is the provision of a delivery handle arrangement that optionally includes a luer tree that is coupled to the alignment knob, wherein the luer tree includes a flush port, a guidewire lumen that is configured to receive a guidewire, and/or a balloon inflation port.

In another and/or alternative non-limiting object of the present disclosure is the provision of a delivery handle arrangement that optionally includes a) a hypotube that is at least partially contained within the inner core, wherein the hypotube is configured to allow flush fluid to flow over the balloon catheter and into the flexible catheter, and b) a sealing arrangement (e.g., an O-ring, etc.) that creates a sliding hemostatic seal between an inner surface of the inner core and an outer surface of the hypotube.

In another and/or alternative non-limiting object of the present disclosure is the provision of a delivery handle arrangement that is used with a prosthetic valve or other type of medical device.

In another and/or alternative non-limiting object of the present disclosure is the provision of a system that delivers an expandable medical device to a treatment site, and wherein the system includes a) a flexible catheter, b) a balloon catheter that is at least partially disposed coaxially within the flexible catheter, c) a delivery handle arrangement, and wherein the delivery handle arrangement includes i) a housing that has an inner core that extends linearly between a proximal end and a distal end of the housing, wherein the inner core at least partially receives the flexible catheter and the balloon catheter, ii) an adjustment mechanism that is configured to control a position of the balloon catheter relative to the flexible catheter, and wherein the adjustment mechanism includes A) a control knob having a connection arrangement (e.g., a plurality of threads, etc.), and B) a shaft (e.g., a threaded shaft, etc.) and/or hypotube that is configured to translate linearly within the housing, and iii) a switch that is configured to lock or unlocked the adjustment mechanism.

In another and/or alternative non-limiting object of the present disclosure is the provision of a system that delivers an expandable medical device to a treatment site, and wherein the system includes a flex mechanism that is configured to controllably bend the distal region flexible catheter, and wherein the flex mechanism includes i) a flex knob that is coupled to a body (e.g., a threaded body, etc.), and wherein the body is at least partially contained within the housing, ii) an insert (e.g., a threaded insert, gear, etc.) that is engaged with the body, c) an actuation insert that optionally has a crimp band; and d) a wire member that is coupled to the flexible catheter and the actuation insert, and wherein rotation of the flex knob in a first direction causes the insert and the actuation insert to translate linearly along the body from or near the distal end towards the proximal end, and wherein the wire member pulls the flexible catheter to bend the flexible catheter at one or more predetermined angles.

In another and/or alternative non-limiting object of the present disclosure is the provision of a system that delivers an expandable medical device to a treatment site, and wherein the system includes a rotational mechanism that is configured to rotate the balloon catheter relative to the flexible catheter, and wherein the rotational mechanism includes i) an alignment knob that is coupled to the hypotube or shaft (e.g., a threaded shaft, etc.) of the longitudinal adjustment mechanism, and ii) a gear, and wherein rotation of the alignment knob in a first direction causes the balloon catheter to rotate relative to the flexible catheter.

In another and/or alternative non-limiting object of the present disclosure is the provision of a system that delivers an expandable medical device to a treatment site, and wherein the system includes a longitudinal adjustment mechanism, and wherein when the longitudinal adjustment mechanism is locked then a) a catch is positioned in the locked position, and b) the catch is engages or causes engagement with the shaft or hypotube, and wherein rotation of the control knob in a first direction causes the engagement arrangement (e.g., the plurality of threads, etc.) to engage the hypotube or shaft (e.g., the threaded shaft, etc.) and translate the hypotube or shaft linearly from or near the proximal end towards the distal end within the housing, and wherein rotation of the control knob in a second direction causes the hypotube or shaft to translate linearly from or near the distal end towards the proximal end.

In another and/or alternative non-limiting object of the present disclosure is the provision of a system that delivers an expandable medical device to a treatment site, and wherein the system includes a longitudinal adjustment mechanism, and wherein when the longitudinal adjustment mechanism is unlocked then a) the catch is positioned in the unlocked position, and b) the catch is disengaged from the shaft or hypotube or from the engagement arrangement (e.g., the plurality of threads, etc.), and wherein the alignment knob of the rotational mechanism is pushed to advance the hypotube or shaft (e.g., the threaded shaft, etc.) towards the distal end, and wherein the alignment knob is pulled to retreat the shaft or hypotube towards the proximal end.

In another and/or alternative non-limiting object of the present disclosure is the provision of a system that delivers an expandable medical device to a treatment site, and wherein the system includes a commissural alignment feature that can be used to rotate the balloon catheter and achieve alignment of the medical device (e.g., commissural posts of the prosthetic valve to the commissures of the native aorta, etc.) at the treatment site.

In another and/or alternative non-limiting object of the present disclosure is the provision of a system that delivers an expandable medical device to a treatment site, and wherein the system includes a fine positioning feature that allows for movement of the balloon catheter in relation of the flexible catheter.

In another and/or alternative non-limiting object of the present disclosure is the provision of a system that delivers an expandable medical device to a treatment site, and wherein the system includes a flex indicator and flex indicator window, wherein the flex indicator is configured to move within the flex indicator window to indicate the degree of flex of the catheter and/or balloon catheter and/or distal region of the flexible catheter.

In another and/or alternative non-limiting object of the present disclosure is the provision of a system that delivers an expandable medical device to a treatment site, and wherein the system includes various balloon catheter features such as a) a stylet that is configured to protect the guidewire lumen prior to use, b) a nose cone that is configured to provides a bonding site for the distal balloon bond, and/or to creates a rigid tapered leading edge for the balloon to cross the annulus, c) a balloon that is configured to be an expansion mechanism for the medical device, d) a guidewire lumen that is configured to form a lumen that spans the most or all of the catheter thereby allowing the medical device to be slid over a guide wire, and thereby guiding the medical device to the intended position at the treatment site (e.g., heart, etc.), e) one or more marker bands that are configured to be visual indicators to position the medical device on the balloon, f) an inflation spring that is configured to facilitate even expansion of the inflatable balloon during inflation of the inflatable balloon, g) a fluid passageway that is configured to form a pathway for saline and/or other liquids or fluids to enter the inflation balloon and cause expansion of the inflation balloon, h) a medical device support that is configured to provide support for the medical device (e.g., prosthetic valve, etc.) as it travels to the treatment site (e.g., aorta, etc.), i) a flexible catheter that is configured to house at least a portion of the balloon catheter, and wherein the flexible catheter can be configured to be flexed to maneuver a medical device around the aortic arch or other regions of the heart or other treatment areas.

In another and/or alternative non-limiting object of the present disclosure is the provision of a delivery handle arrangement that facilitates a delivery of a medical device to a treatment site; the delivery handle arrangement comprises a) a housing having an inner core that at least partially extends linearly between a proximal end and a distal end of the housing; and wherein the inner core at least partially receives hypotube; b) a flexible catheter and a balloon catheter; a proximal region of the flexible catheter is connected to the housing; the balloon catheter is movable within the flexible catheter; a distal region of the hypotube is connected to a proximal region of the balloon catheter; c) a longitudinal adjustment mechanism that is configured to control longitudinal movement of the hypotube; and wherein the longitudinal adjustment mechanism includes i) a control knob that is movable relative to the housing; and ii) a switch that is configured to move between a lock or unlocked position; and wherein the hypotube is only movable linearly within the housing when the longitudinal adjustment mechanism is in the locked position and the control knob is moved; and wherein the hypotube is movable linearly within the housing when the longitudinal adjustment mechanism is in the unlocked position and without requiring movement the control knob.

In another and/or alternative non-limiting object of the present disclosure is the provision of a delivery handle arrangement wherein the control knob is rotatable about a longitudinal axis of the housing.

In another and/or alternative non-limiting object of the present disclosure is the provision of a delivery handle arrangement wherein the control knob includes a first stop region and a second stop region that are spaced from one another; the switch is positioned between the first stop region and the second stop region.

In another and/or alternative non-limiting object of the present disclosure is the provision of a delivery handle arrangement wherein the longitudinal adjustment mechanism further includes a movable catch, a threaded insert and insert biasing arrangement; the switch includes a channel having a first stop and a second stop; the first stop has a larger width than the second stop; the catch is positioned at the first stop when the switch is moved to the unlocked position; the catch positioned at the second stop when the switch moves to the locked position; the biasing arrangement is configured to bias the catch upwardly in the channel at the first stop when the switch is moved to the unlocked position; the channel is configured to cause the catch to move downwardly when the switch is moved from the unlocked position to the locked position; the downward movement of the switch is configured to cause the threaded insert to move downwardly and engage a threaded shaft; the threaded shaft is connected to the hypotube.

In another and/or alternative non-limiting object of the present disclosure is the provision of a delivery handle arrangement wherein rotation of the control knob in a first direction causes the shaft to move linearly from or near the proximal end towards the distal end within the housing when the switch is in the locked position; wherein rotation of the control knob in a second opposite direction causes the shaft to move linearly from or near the distal end towards the proximal end when the switch is in the locked position; and wherein rotation of the control knob does not cause the shaft to move linearly between the distal end and proximal end when the switch is in the unlocked position.

In another and/or alternative non-limiting object of the present disclosure is the provision of a delivery handle arrangement wherein the longitudinal adjustment mechanism further includes a fine alignment sleeve; the control knob includes a threaded body positioned in the housing; the fine alignment sleeve positioned in the housing and movable along a longitudinal axis of the housing; the fine alignment sleeve includes a threaded region that threadedly engages the threaded body; the control knob is configured to move the fine alignment sleeve along the longitudinal axis of the housing when the control knob is rotated; the longitudinal axis of the housing includes a compression flange that is configured to releasably engage and disengage from the hypotube or sleeve on the hypotube; the switch in the locked position causes the compression flange to releasably engage the hypotube or sleeve on the hypotube; the switch in the unlocked position causes the compression flange to disengage the hypotube or sleeve on the hypotube.

In another and/or alternative non-limiting object of the present disclosure is the provision of a delivery handle arrangement wherein rotation of the control knob in a first direction causes the fine alignment sleeve to move linearly from or near the proximal end towards the distal end within the housing when the switch is in the locked position; wherein rotation of the control knob in a second opposite direction causes the fine alignment sleeve to move linearly from or near the distal end towards the proximal end when the switch is in the locked position; and wherein rotation of the control causes the fine alignment sleeve to move linearly between the distal end and proximal end when the switch is in the unlocked position and does not cause the hypotube to move linearly between the distal end and proximal end.

In another and/or alternative non-limiting object of the present disclosure is the provision of a delivery handle arrangement further comprising a flex adjustment mechanism that is configured to controllably bend or flex a distal region of the flexible catheter; the flex mechanism includes i) a flex knob that is movably connected to the housing; the flex knob includes a body portion that is at least partially positioned in the inner core of the housing; ii) a flex insert that is at least partially positioned in the housing; the flex insert is in engagement with the body portion; the flex insert is caused to move by movement of the flex knob; iii) an actuation insert that is at least partially positioned in the housing; the actuation insert is in engagement with the body portion of the flex knob and/or the flex inert; the actuation insert is caused to move by movement of the flex knob and/or the flex insert; and iv) a wire member; the wire member is coupled at a proximal end to the flex insert and/or the actuation insert and at a distal end to a distal region of the flexible catheter; and wherein the distal region of the flexible catheter is caused to controllably bend during movement of the flex knob.

In another and/or alternative non-limiting object of the present disclosure is the provision of a delivery handle arrangement wherein the flex knob is configured to rotate on the housing; the flex knob is configured to cause a portion of the wire member to be drawn into the housing when rotated in a first direction, and wherein the distal region of the flexible catheter is caused to bend when the flex knob is rotated in the first direction; the flex knob is configured to cause the wire member to be moved outwardly from the housing when rotated in a second direction, and wherein the distal region of the flexible catheter is caused to unbend when the flex knob is rotated in the second direction.

In another and/or alternative non-limiting object of the present disclosure is the provision of a delivery handle arrangement further including a first flex indicator arrangement located on the housing; the first flex indicator arrangement includes a first flex indicator that is configured to provide information to a user about a degree or amount of bending of the distal portion of the flexible catheter prior, during and/or after the flex knob is rotated.

In another and/or alternative non-limiting object of the present disclosure is the provision of a delivery handle arrangement wherein the first flex indicator arrangement includes a flex indicator window on an outer surface of the housing and wherein the a first flex indicator is covered by the flex indicator window.

In another and/or alternative non-limiting object of the present disclosure is the provision of a delivery handle arrangement wherein the first flex indicator includes a movable needle and a flex bend graphic; and wherein the needle translates along the housing and along a portion of the flex bend graphic to indicate to a user a degree of bending of the distal region of the flexible catheter.

In another and/or alternative non-limiting object of the present disclosure is the provision of a delivery handle arrangement wherein the first flex indicator is located rearwardly of the flex knob.

In another and/or alternative non-limiting object of the present disclosure is the provision of a delivery handle arrangement further including a second flex indicator arrangement; the second flex indicator arrangement includes a second flex indicator; the second flex indicator is positioned on an opposite side of the housing from the first flex indicator.

In another and/or alternative non-limiting object of the present disclosure is the provision of a delivery handle arrangement wherein the flex knob does not move along a longitudinal axis of the housing wherein the flex knob is moved on the housing.

In another and/or alternative non-limiting object of the present disclosure is the provision of a delivery handle arrangement wherein the distal end of the flexible catheter includes a pull ring; the wire member is connected to the pull ring; the pull ring is spaced from a distal end of the flexible catheter.

In another and/or alternative non-limiting object of the present disclosure is the provision of a delivery handle arrangement wherein the distal portion of the flexible catheter includes a flexible hypotube or spring; the flexible hypotube or spring is configured to a) bend when the distal portion of the flexible catheter is caused to bend by the guide flex arrangement, and b) cause the distal portion of the flexible catheter to unbend when the guide flex arrangement allows the distal portion of the flexible catheter to unbend from a bent position the flexible hypotube or spring is positioned further from the distal end of the flexible catheter than the pull ring.

In another and/or alternative non-limiting object of the present disclosure is the provision of a delivery handle arrangement wherein the distal portion of the flexible catheter includes the flexible hypotube; the flexible hypotube is a laser cut hypotube.

In another and/or alternative non-limiting object of the present disclosure is the provision of a delivery handle arrangement further comprising a rotational mechanism that is configured to rotate the balloon catheter relative to the flexible catheter; the rotational mechanism includes an alignment component that engages the hypotube: rotation of the alignment component about a longitudinal axis of the housing is configured to cause the hypotube to rotate about the longitudinal axis of the housing; and wherein rotation of the hypotube causes the balloon catheter to rotate within the flexible catheter.

In another and/or alternative non-limiting object of the present disclosure is the provision of a delivery handle arrangement wherein the alignment mechanism is configured to advance a distal end of the hypotube toward and away from the distal end of the housing.

In another and/or alternative non-limiting object of the present disclosure is the provision of a delivery handle arrangement wherein the alignment component is an alignment knob arrangement that includes an alignment knob, an inner cap, a gear tooth, and a biasing arrangement; the gear tooth is biased into engagement with the inner cap by the biasing arrangement; an end of the gear tooth is configured to engage flexible engagement flanges on the inner cap to cause the flexible engagement flanges to engage an outer surface of the hypotube or sleeve about the hypotube.

In another and/or alternative non-limiting object of the present disclosure is the provision of a delivery handle arrangement wherein the alignment mechanism is configured to advance a distal end of the hypotube toward and away from the distal end of the housing only when the switch is in the unlocked position; the alignment mechanism is configured to rotate the hypotube when the switch is in either the locked or unlocked position.

In another and/or alternative non-limiting object of the present disclosure is the provision of a delivery handle arrangement wherein the alignment component is an a luer tree that is connected to the hypotube.

In another and/or alternative non-limiting object of the present disclosure is the provision of a delivery handle arrangement wherein the alignment mechanism is configured to advance a distal end of the hypotube toward and away from the distal end of the housing only when the switch is in the unlocked position; the alignment mechanism is configured to only rotate the hypotube when the switch is in the unlocked position.

In another and/or alternative non-limiting object of the present disclosure is the provision of a delivery handle arrangement further comprising a luer tree; the luer tree includes one or more of a flush port, a guidewire lumen that is configured to receive a guidewire, and/or a balloon inflation port.

In another and/or alternative non-limiting object of the present disclosure is the provision of a delivery handle arrangement wherein the hypotube is configured to allow flush fluid to flow at least partially over the balloon catheter and at least partially into the flexible catheter; and wherein a sealing arrangement is configured to creates a sliding hemostatic seal between outer surface of the hypotube and one or more components in the housing.

In another and/or alternative non-limiting object of the present disclosure is the provision of a delivery handle arrangement wherein the medical device is a prosthetic valve.

These and other objects and advantages will become apparent to those skilled in the art upon reading and following the description taken together with the accompanying drawings.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein.

DETAILED DESCRIPTION OF NON-LIMITING EMBODIMENTS

Figure 1:
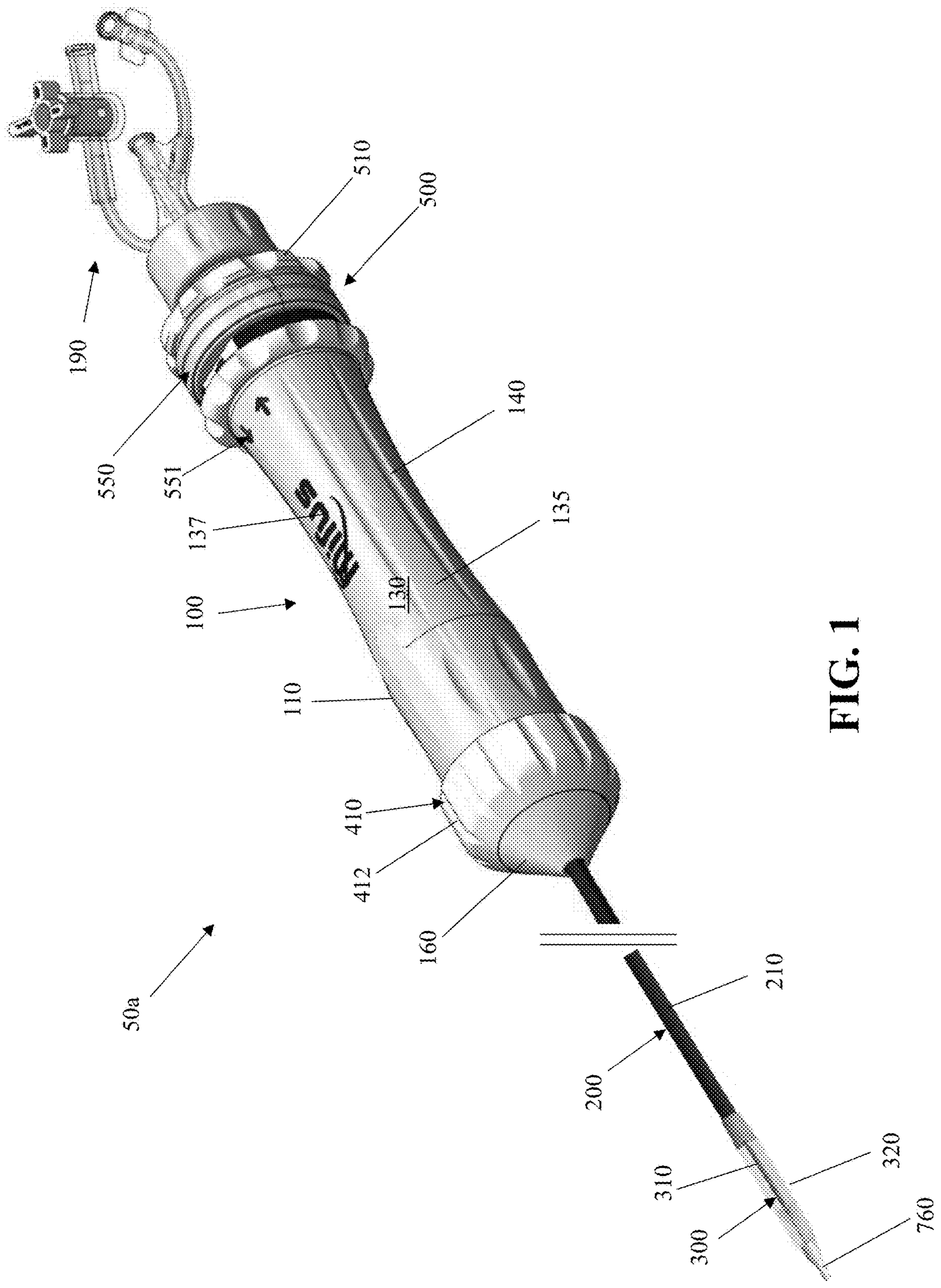
FIG. 1 depicts an exemplary, non-limiting delivery system comprising a non-limiting delivery handle arrangement in accordance with the present disclosure.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values and all ranges therebetween).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

Example implementations of the disclosed technology generally provides a medical device that can includes a prosthetic valve (e.g., heart valve, TAVR valve, mitral valve replacement, tricuspid valve replacement, pulmonary valve replacement, etc.) and a delivery system for delivering the prosthetic valve to a treatment site (e.g., in a patient's heart valve, etc.). More particularly, example implementations of the disclosed technology provides a delivery handle arrangement that is configured to more accurately deliver such prosthetic valves to the treatment site. As can be appreciated, the delivery handle arrangement can be used to delivery other types of medical devices to a treatment site (e.g., LAA (left atrial appendage) closure devices, stent, etc.).

The delivery handle arrangement 100 in arrangement with the present disclosure includes: (i) a flex mechanism that is configured to facilitate in bending or flexing a distal region of the flexible catheter (e.g., flex or bend the distal region of the flexible catheter around various bends or arches [e.g. aortic arch bend], etc.) and to adjust alignment of the medical device at a treatment site (e.g., obtain coaxial alignment of the crimped prosthetic valve with the aortic annulus prior to expansion of the prosthetic valve, etc.); (ii) a longitudinal adjustment mechanism that is configured to advance or retract the balloon catheter's axial position relative to the flexible catheter; and (iii) a commissure alignment mechanism that is configured to rotate the balloon catheter so as to properly orient the medical device at a treatment site (e.g., rotate a crimped prosthetic valve and control the rotational orientation of the prosthetic valve leaflet attachment points (commissure) relative to the native anatomical valve of the heart prior to the expansion of the prosthetic valve at the treatment site, etc.). In one non-limiting arrangement, the longitudinal adjustment mechanism can advantageously be transitioned using a switch between a locked position for fine longitudinal movement of the balloon catheter relative to the flexible catheter, and an unlocked position for larger longitudinal movement of the balloon catheter relative to the flexible catheter.

When the medical device is a prosthetic valve, the prosthetic valve is not limited to a TAV, but can be mitral valve replacement, tricuspid valve replacement, pulmonary or valve replacement. The prosthetic valve includes a radially collapsible and expandable frame and a leaflet structure comprising a plurality of leaflets. The prosthetic valve can optionally include an outer skirt disposed on at least a portion of an outer surface of the expandable frame and overlying a plurality of cells of at least a portion of the frame. The prosthetic valve can also or alternatively include an inner skirt. The expandable frame can optionally comprise a plurality of interconnected struts and strut joints defining a plurality of open cells in the expandable frame. As can be appreciated, the expandable frame can have other configurations. The expandable frame is optionally partially (e.g., 1-99.999 wt. % and all values and ranges therebetween) or fully made of a metal material.

One non-limiting implementation of the delivery system 50*a* of the subject application will now be described with reference to the attached FIGS. 1-4, wherein like reference numerals are used to refer to like elements throughout.

Figure 2:
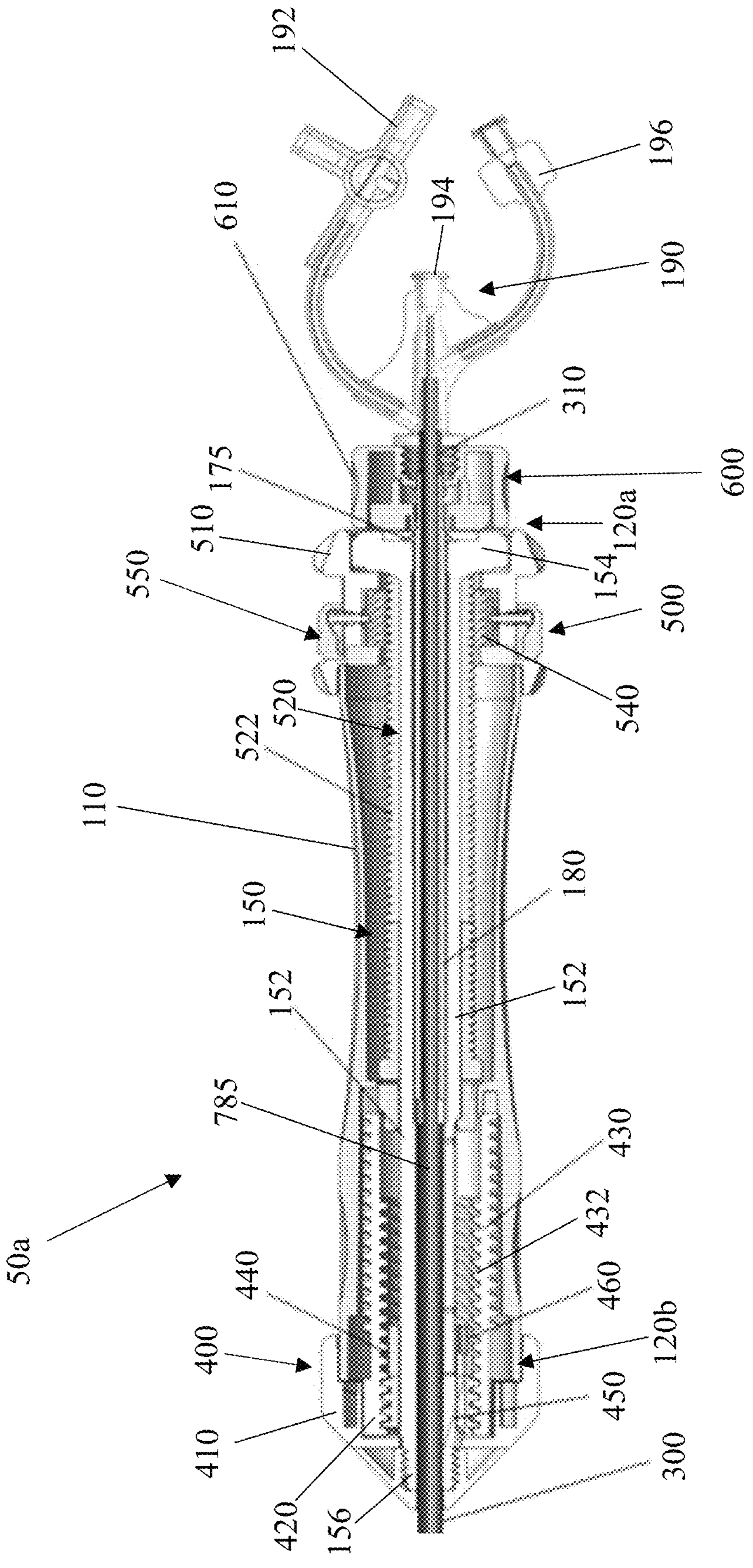
FIG. 2 is a cross-sectional side view of the delivery handle arrangement of FIG. 1 wherein the delivery handle arrangement is configured in an unlocked position.
Figure 3:
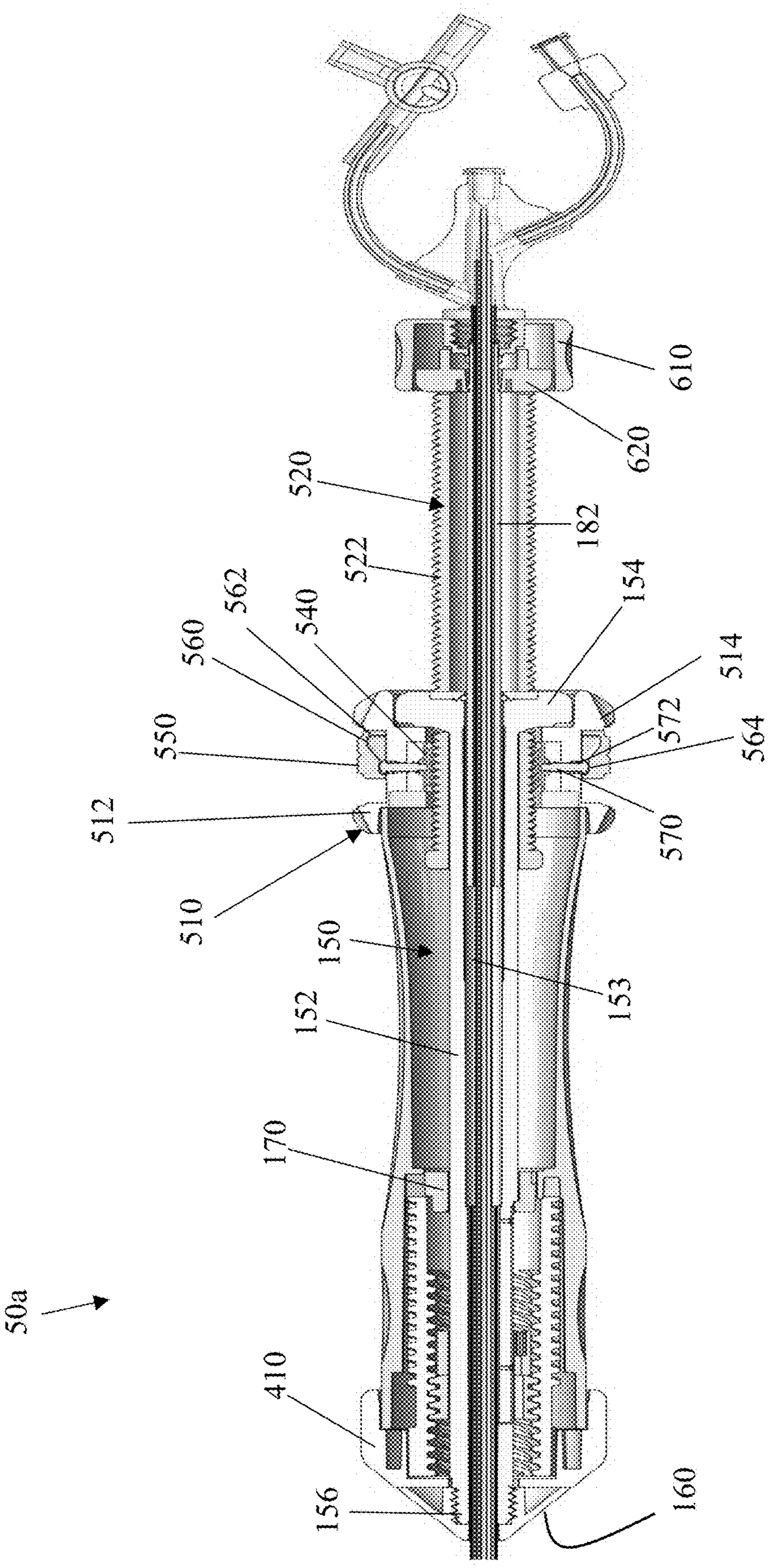
FIG. 3 is a cross-sectional side view of the delivery handle arrangement of FIG. 1, wherein the delivery handle arrangement is configured in a locked position.
Figure 4:
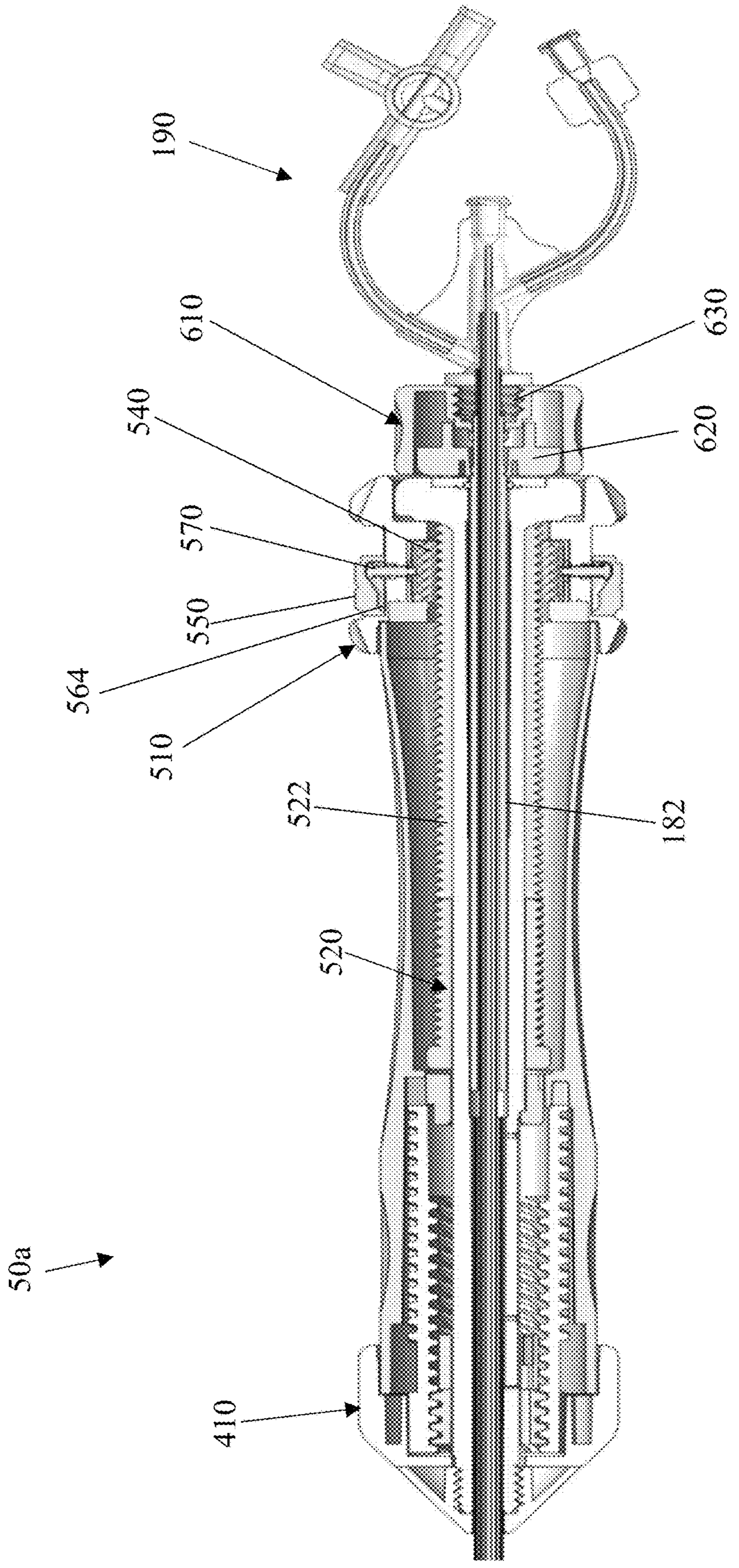
FIG. 4 is another cross-sectional side view of the delivery handle arrangement of FIG. 1 wherein the delivery handle arrangement is configured in an unlocked position.

FIG. 1 depicts an exemplary, non-limiting delivery system 50*a* comprising a non-limiting handle arrangement 100. FIGS. 2 and 4 are cross-sectional side views of the delivery handle arrangement 100 of FIG. 1, wherein the delivery handle arrangement 100 is configured in an unlocked position. FIG. 3 is a cross-sectional side view of the delivery handle arrangement 100 of FIG. 1, wherein the delivery handle arrangement 100 is configured in a locked position.

With reference to FIGS. 1-4, there is provided a delivery system 50*a* that is configured for use with a medical device (e.g., prosthetic valve, stent, etc.). The delivery system 50*a* includes a delivery handle arrangement 100, a flexible catheter or similar flexible guide catheter 200, and a balloon catheter 300 disposed coaxially within the flexible catheter 200. The flexible catheter 200 includes a flexible shaft 210. The balloon catheter 300 includes a shaft 310 and an inflatable balloon 320.

The delivery handle arrangement 100 includes an elongated housing 110 having a proximal end 120*a* and a distal end 120*b*. The housing 110 is a generally circular cross-sectional shape along a longitudinal axis of the housing 110; however, other shapes can be used. The cross-sectional area of the housing 110 can optionally vary along the longitudinal length of the housing 110. For example, in the present non-limiting embodiment, the housing 110 has a smaller cross-sectional area in the mid-region of the housing 110, as compared to the regions located at and/or near the proximal and distal ends 120*a*, 120*b*. In the present non-limiting embodiment, the housing 110 has a length that is sufficient for a user to easily grasp the housing 110 with the user's hand (e.g., 4-12 inches and all values and ranges therebetween). The housing 110 further includes a middle handle portion 135 that has an outer surface 130. Outer surface 130 can optionally include one or more ribs 140 formed thereon that are configured to facilitate in the gripping of the middle handle portion 135. The outer surface 130 of the housing 110 can also optionally include one or more orientation markings 137 that can optionally be used by a user to indicate the proper orientation of the delivery handle 110 during use (e.g., proper commissural alignment of medical device at treatment site, proper commissural alignment of prosthetic heart valve at treatment site in heart, etc.). As illustrated in FIG. 1, there is a marking 137 in the form of a "MiRus" logo that is positioned on the handle. This marking can be used as a visual indicator that when the marking is facing upwardly on the handle 110, the handle 110 is in the proper position during a medical device insertion procedure. As can be appreciated, multiple marking can be positioned on the handle 110. The type and number and shape of the one or more markings 137 on the handle are non-limiting.

The housing 110 includes a hollow, internal body cavity 150 that forms the interior cavity of the delivery handle arrangement 100 and is positioned between the proximal end 120*a* and the distal end 120*b* of the housing 110. A body core 152 is positioned in the body cavity and is positioned along the central longitudinal axis of the delivery handle arrangement 100 between the proximal end 120*a* and the distal end 120*b* of the housing 110. The distal end of the body core 152 can optionally include a flange 154 about which a portion of a proximal portion is control knob 510 is positioned about. The body core 152 has a passageway that extends along the longitudinal length of the body core and at least a portion of the hypotube 190 is movable positioned in the passageway. Generally, the passageway is positioned along the central longitudinal axis of the housing; however, this is not required. Generally, the body core 152 is fixed in position in the body cavity 150; however, this is not required. As illustrated in FIGS. 2-4, the flange includes an opening that allows the threaded shaft 520 can move therethrough.

The outer surface of the flexible catheter shaft 210 is fixed or otherwise connected to the inner surface of the body cavity 150 at or near the distal end 120*b* of the housing 110. In one non-limiting aspect of the present disclosure, the flexible catheter shaft 210 is fixed to the body cavity 150 with an adhesive; however, other connection arrangements can be used (e.g., melted connection, clamp or other type of mechanical connection, etc.). As will be discussed in more detail below, the proximal end of the balloon catheter 300 is connected to the distal end or end region of hypotube 180.

A portion of the balloon catheter 300 and shaft 310 extend coaxially through the flexible catheter shaft 210 and a movable relative to the flexible catheter shaft 210. The flexible catheter 200 and the balloon catheter 300 extend outwardly from the distal end 120*b* of the housing 110.

The delivery handle arrangement 100 includes a flex mechanism 400, a longitudinal adjustment mechanism 500, and/or a commissure alignment (CA) mechanism 600.

The flex adjustment mechanism 400 is located near the distal end 120*b* of the housing 110, the longitudinal adjustment mechanism 500 is located near the proximal end 120*a* of the housing 110, and the CA mechanism 600 is also located near the proximal end 120*a* of the housing 110.

The flex adjustment mechanism 400 is configured to cause controlled bending of a distal portion of flexible catheter 200. The flex adjustment mechanism includes a flex knob 410 that is positioned on the housing 110 of the delivery handle arrangement 100. The flex knob 410 is configured to be moved by a user (e.g., flex knob can be rotated by a user, flex knob can be slid on the housing by a user, etc.) to enable the user to controllably bend a distal portion of the flex catheter 200. As can be appreciated, the flex knob can be located on other regions of the housing 210. As also can be appreciated, the flex knob 230 can be substituted by other components (e.g., flex switch, flex button, flex tab, electronic flex switch mechanism, etc.). As illustrated in FIGS. 2-4, the flex knob 410 is generally is rotatably connected to the housing 110 such that the flex knob 410 rotates about a central longitudinal axis of the housing 110. As illustrated in FIGS. 2-4, the flex knob 410 is rotatably connected to the ribbed portion 156 on the distal end of the body core 152. As can be appreciated, other connection arrangements can be used.

The flex knob 410 includes a body portion 430 that is partially or fully located in within the body cavity 150 of the housing 110; and wherein the body portion 430 of the flex knob is configured to engage a flex insert and/or flex actuator 440 that is partially or fully located within the body cavity 150 of the housing 110. The body portion 430 of the flex knob optionally includes a plurality of threads. The threads are configured to engage flex insert and/or flex actuator 440. As flex knob is rotated by a user, the flex knob causes direct or indirect the movement of the flex insert and/or flex actuator 440 forwardly along the longitudinal axis of the housing when the flex knob is rotated in one direction, or cause rearward movement of the flex insert and/or flex actuator along the longitudinal axis of the housing when the flex knob is rotated in the opposite direction. As can be appreciated, the flex insert and/or flex actuator 440 can be separate components or a single component. In one non-limiting arrangement, a) the flex insert includes threading such that when the flex knob is rotated, the flex insert remains in position and does not move along the longitudinal axis of the housing, and b) the flex actuator 440 includes threading such that when the flex knob is rotated, the flex actuator is caused to move along the longitudinal axis of the housing, and wherein the wire member 450 is connected to the flex actuator.

The flex insert and/or flex actuator 440 is connected to wire member (e.g., pull-wire) 450 via a crimp band 460; and wherein the wire member 450 is positioned in at least a portion of the flex catheter 200; and wherein the wire member 450 is moveable relative to an outer surface of the flex catheter 200; and wherein movement of the flex insert and/or flex actuator 440 causes the wire member 450 to move relative to the outer surface of the flex catheter 200; and wherein movement of the wire member 450 causes a distal portion of the flex catheter 200 to controllably bend and unbend. The flex insert and/or flex actuator 440 that is located partially or fully within the housing 110 and can be configured to not rotate within the housing, but to only move along a longitudinal axis of the housing 110. The flex knob 410 can optionally includes one or more grip members 412 (e.g., grooves, rough surface, slots, ribs, etc.) to facilitate in gripping and/or moving of the flex knob 410.

The flex adjustment mechanism 400 optionally includes flex indicator to indicate a degree/amount of flex at the distal portion of the flex catheter 200. The flex indicator, when used, can include one or more of a needle indicator, digital/electronic indicator, visual indicator, color indicator, sound indicator, bar indicator, light indicator, etc. to provide information to the user of the degree and/or amount of bending of the distal portion of the catheter. In one non-limiting configuration, the flex indicator includes a needle indicator, digital indicator, or bar indicator that is configured to move as the flex insert 440 and/or other component of the delivery handle arrangement moves relative to the housing 110 so as to indicate to a user a degree of flex that is present at the distal portion of the flexible catheter 200. The flex indicator can optionally include numbers, letters, bars, sloped graphics, shapes, or other markings to provide the user additional information on the degree or amount of flex in the flexible catheter 200. The outer portion of the housing 110 can optionally include one or more indicator windows. The one or more indicator windows can include a partially or fully transparent material covering (e.g., clear plastic, clear glass, etc.) to enable a user to see through the partially or fully transparent material covering and into indicator window to view of the flex indicator.

When the knob 410 is rotated in a first direction (either clockwise or counterclockwise), the flex actuation insert 440 is caused to translate axially along the knob body 430, thereby pulling the wire 450 and causing the flexible catheter 200 to flex the flexible catheter 200.

In one non-limiting example of the present disclosure, rotating the knob 410 in a first direction (either clockwise or counterclockwise) causes the threaded insert 430 and the flex actuation insert 440 to translate along the knob body 420 from the distal end 120*b* towards the proximal end 120*a*, thereby pulling the wire 450 and causing the distal region of the flexible catheter 200 to flex or displace by a predetermined angle. The flex adjustment mechanism 400 is configured to only move wire 450, and does not cause longitudinal or rotational movement of the balloon catheter 300 relative to the flexible catheter 200.

In operation of the flex adjustment mechanism, the flexible catheter is inserted into a vascular passageway (e.g., blood vessel, etc.) until the distal region of the flexible catheter reaches the treatment site. The pathway to the treatment site is not always straight. In regions of the vascular passageway where the pathway curves more than 20°, the proximal end of the flexible catheter may damage the inner wall of the vascular passageway as the flexible catheter is moved through such curved pathway. The flex adjustment mechanism on the delivery system of the present disclosure can be used to inhibit or prevent such damage to the inner wall of the vascular passageway as the flexible catheter is moved through such curved pathway. When the distal end of the flexible catheter reaches the curved passageway, a user can move or rotate the flex knob on the housing of the delivery handle so as to cause the wire member to move within the flexible catheter. As discussed above, such movement of the wire member causes the distal region of the flexible catheter to bend and unbend. The user can control the amount of movement or rotation of the flex knob to obtain the desired bending of the flexible catheter. A user can rotate the delivery handle, which in turn causes the rotation of the flexible catheter. Such rotation of the flexible catheter facilitates in orienting the flexible catheter in the vascular passage to obtain the desired bending direction of the distal region of the flexible catheter when the flex knob is moved or rotated. After the distal region of the flexible catheter has passed through a curved region in the vascular passageway, the user can move or rotate the flex knob to cause the distal region of the flexible catheter to unbend. As can be appreciated, the movement or rotation of the flex knob and/or the rotation of the flexible catheter by the delivery handle can be used to proper position the medical device at the treatment site (e.g., center the expandable medical device at the treatment site, ensure proper commissural alignment of the medical device at the treatment site, etc.).

Figure 5B:
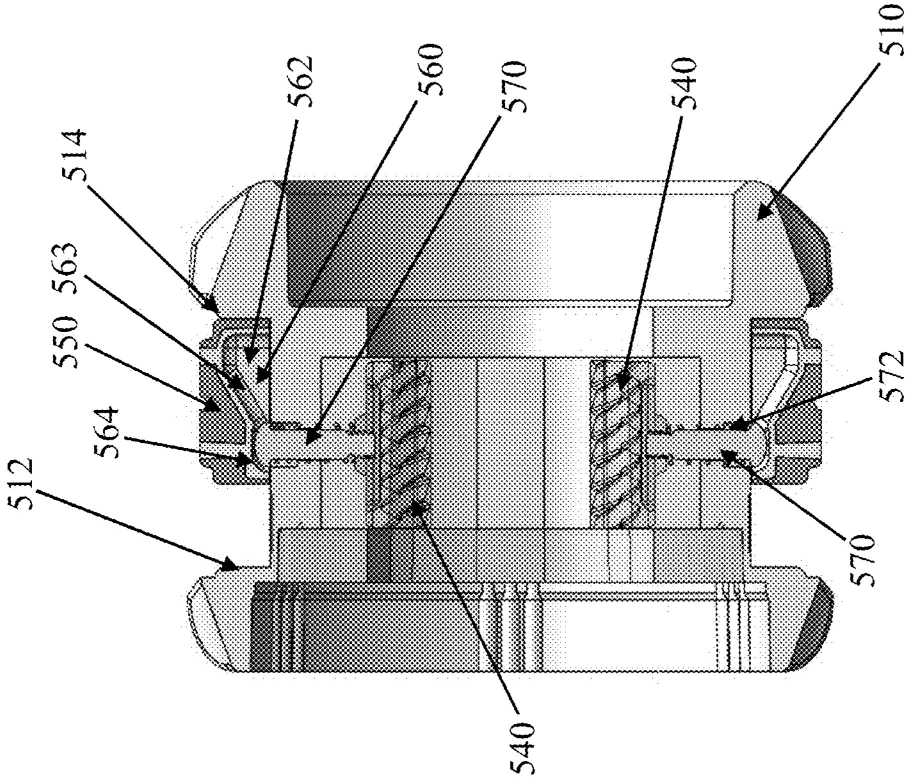
FIGS. 5A and 5B are a side view and a cross-sectional view of a portion of the delivery handle arrangement that illustrates the positioning switch and components of the positioning switch of the longitudinal adjustment mechanism.
Figure 5A:
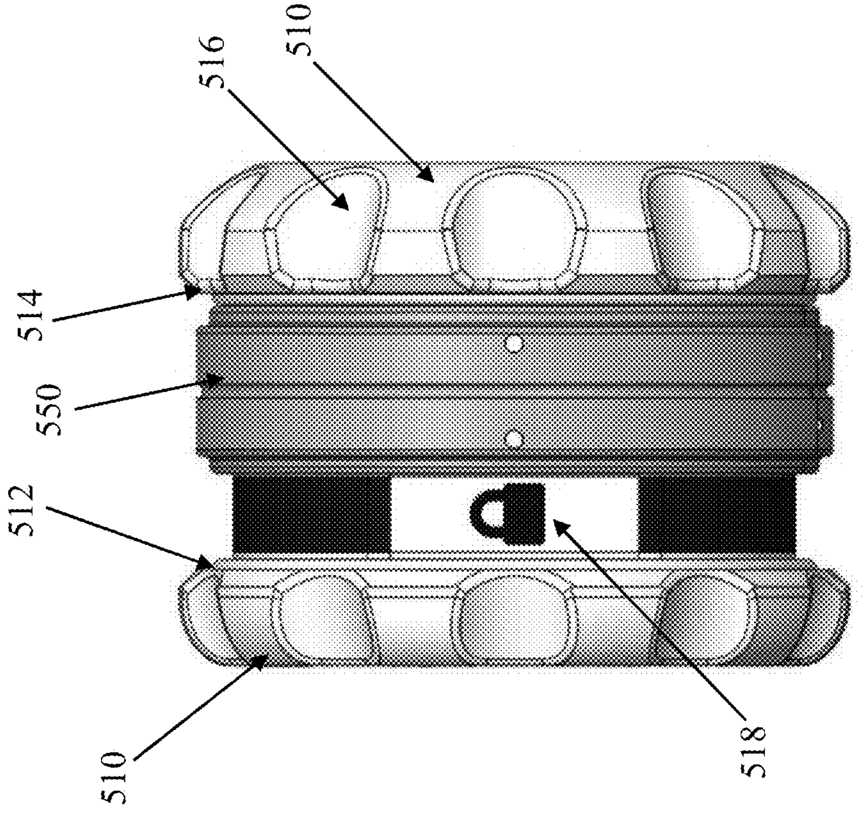

Referring now to FIGS. 1-5B, the longitudinal adjustment mechanism 500 is configured to move the balloon catheter 300 longitudinally relative to the flexible catheter 200. The longitudinal adjustment mechanism 500 includes a control knob 510 having a first stop region 512, a second stop region 514 on the outer surface of the control knob. The control knob 510 has a cavity through the longitudinal axis of the control knob, and the central longitudinal axis of the control knob is generally aligned with the central longitudinal axis of housing 110 and threaded shaft 520 that includes threading 522 on the outer surface of the threaded shaft 520. The longitudinal adjustment mechanism 500 is transitionable between a locked position as illustrated in FIGS. 3 and 5A and an unlocked position as illustrated in FIGS. 2, 4 and 5B by way of a switch 550. The switch 550 is positioned and is movable between the first stop region 512 and the second stop region 514 of the control knob 510. Optional indicators, words or symbols 551 can be positioned on the housing or longitudinal adjustment mechanism to indicate the located and unlocked position and/or provide information on how to the switch. The outer surface of the control knob can optionally include divots 516, ribs, rough surface to facilitate in the gripping and/or rotating of the control knob 510. A portion of the outer surface of the longitudinal adjustment mechanism 500 can optionally include a visual indicator 518 (e.g., lock symbol or other type of symbol or graphic, color, etc.) to indicate whether the control knob is in the locked or unlocked position.

The lower portion of switch 550 includes a channel 560 formed therein that is configured to receive a portion of a catch or pin 570. The catch or pin 570 is configured to be moveable within the channel 560. Channel 560 includes a first stop 562 and a second stop 564. The first stop 562 has a greater width or height than that of the second stop 564. The catch or pin 570 is biased upwardly from shaft 520 by spring 572; however, other biasing mechanisms can be used. When the switch 550 is in the unlocked position as illustrated in FIGS. 2 and 4, the spring 572 causes the catch or pin 570 to move upwardly and away from shaft 520. The larger width of the first stop region 562 allows the catch or pin 570 to move upwardly when the switch 550 is moved to the uplocked position. When the switch moves to the locked position as illustrated in FIG. 3, the sloped channel region 563 between the first stop region 562 and the second stop region 564 causes the catch or pin 570 to move downwardly toward to the shaft 520 until the catch or pin 570 is in the fully lower position when the switch is in the locked position as illustrated in FIG. 3.

The bottom of the catch or pin 570 is configured to engage a plurality of latching threads on a threaded insert 540 (e.g., gear, etc.) that are located in the body cavity 150 of the housing 110. The threaded insert 540 are configured to engage the thread on the outer surface of shaft 520. Shaft 520 is positioned in the body cavity 150 and is configured to move along the longitudinal axis of the housing 110. The shaft 520 is also configured to be rotatable about a longitudinal axis of the housing 110. When the catch or pin 570 is caused to move downwardly, the bottom of the catch or pin causes the threaded insert 540 to engage with the threads on the outer surface of the shaft 520. When the switch 550 is in the locked position, the catch or pin 570 is causes the threaded insert 540 to engage with the threads on the outer surface of the shaft 520 as illustrated in FIG. 3. When the switch 550 is in the unlocked position, the catch or pin 570 is moves upwardly and causes the threaded insert 540 to disengage from the threads on the outer surface of the shaft 520 as illustrated in FIGS. 2 and 4.

As illustrated in FIGS. 2-4, the distal end or region of the shaft 520 is connected to the proximal end or region of the balloon catheter 300. Longitudinal movement of shaft 520 in housing 110 causes longitudinal movement of the balloon catheter 300 relative to the flexible catheter 200. Rotational movement of shaft 520 in housing 110 causes rotational movement of the balloon catheter 300 relative to the flexible catheter 200.

When the longitudinal adjustment mechanism 500 is in the locked position: (i) the catch 570 is positioned at the second stop 564 of the channel 560; (ii) the switch 550 is positioned closer to the second portion 514 of the control knob 510, and (iii) the catch 570 is engaged with the threaded insert 540. In this locked position, the relative axial position between the balloon catheter shaft 310 and the flexible catheter 200 is fixed and cannot be freely moved along the longitudinal axis of the housing other than by rotation of control knob 510, and thus the balloon catheter shaft 310 axial position can be adjusted in a controlled manner by rotating (either clockwise or counterclockwise) the control knob 510. Such controlled longitudinal movement of shaft 520 enables a user to achieve fine longitudinal movement of the shaft 520, when in turn results in fine adjustment of the distal end or region of the balloon catheter 300 at a treatment site so as to ensure proper delivery and placement of the medical device at the treatment site. Rotating the control knob 510 causes the threaded insert 540 to engage the threaded shaft 520, thereby causing the threaded shaft 520 to translate linearly along the longitudinal axis of the housing 110 of the delivery handle arrangement 100. In one non-limiting example of the present disclosure, when the switch 550 is in the locked position, rotating the control knob 510 in a first direction (either clockwise or counterclockwise) causes the threaded shaft 520 to translate linearly from the proximal end 120*a* towards the distal end 120*b*, thereby advancing the balloon catheter 300 relative to the flexible catheter 200. In another non-limiting example of the present disclosure, when the switch 550 is in the locked position, rotating the control knob in a second direction (either clockwise or counterclockwise) causes the axial position threaded shaft 520 to translate linearly from the distal end 120*b* towards the proximal end 120*a*, thereby retracting the balloon catheter 300 relative to the flexible catheter 200.

When the switch 550 of the longitudinal adjustment mechanism 500 is in the unlocked position: (i) the catch 570 is positioned at the first stop 562 of the channel 560; (ii) the switch 550 is positioned closer to the first portion 512 of the control knob 510; and (iii) the catch 570 is disengaged from and/or is not asserting downward pressure on the threaded insert 540, thus the latching threads are partially or fully disengaged from the threaded shaft 520. In this unlocked position, the user can freely advance and retract the balloon catheter 300 within the flexible catheter 200 by manually pushing (e.g., to advance) or pulling (e.g., to retract) the alignment knob 610 and/or the luer tree 190 (discussed in greater detail below) to cause the threaded shaft 520 to move longitudinally along the longitudinal axis of the housing. In the unlocked position, rotation of the control knob 510 does not cause threaded shaft 520 to move longitudinally along the longitudinal axis of the housing. In one non-limiting example of the present disclosure, when the switch 550 is in the unlocked position, pushing the alignment knob 610 and/or the luer tree 190 causes the threaded shaft 520 to translate linearly from the proximal end 120*a* towards the distal end 120*b* of the housing 110, thereby advancing the balloon catheter 300 relative to the flexible catheter 200. In another non-limiting example of the present disclosure, when the switch 550 is in the unlocked position, pulling the alignment knob 610 and/or the luer tree 190 causes the threaded shaft 520 to translate linearly from the distal end 120*b* towards the proximal end 120*a*, thereby retracting the balloon catheter 300 relative to the flexible catheter 200.

Figure 6A:
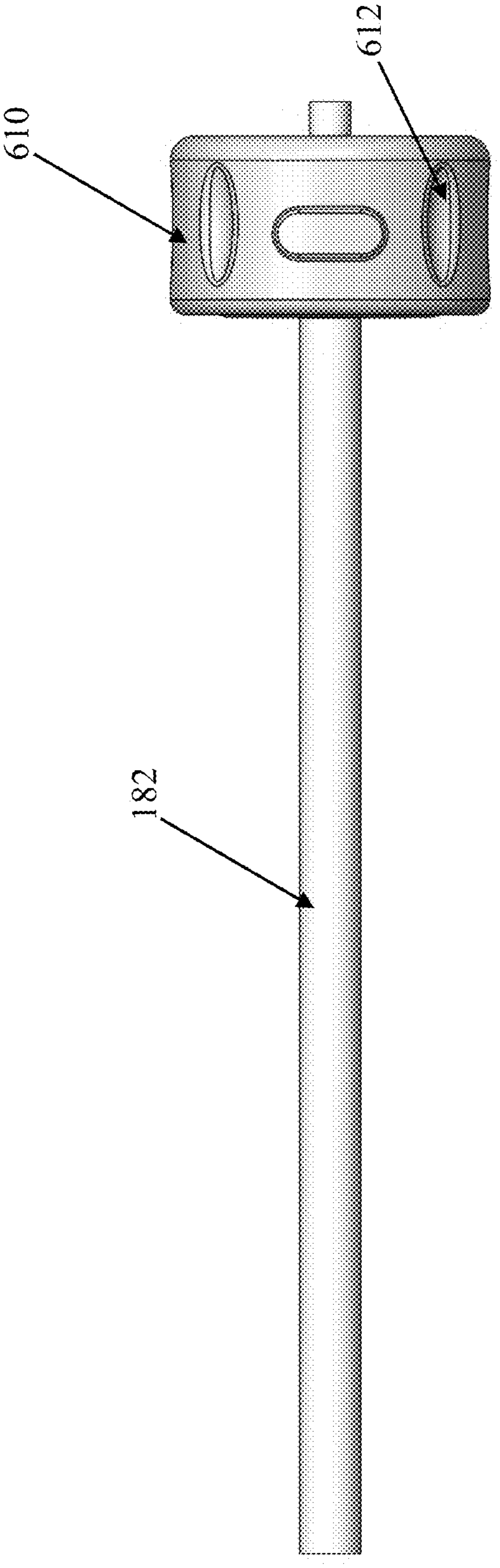
FIGS. 6A and 6B are a side view and a cross-sectional view of a portion of the delivery handle arrangement that illustrates the commissural alignment feature and components of the commissural alignment feature.
Figure 6B:
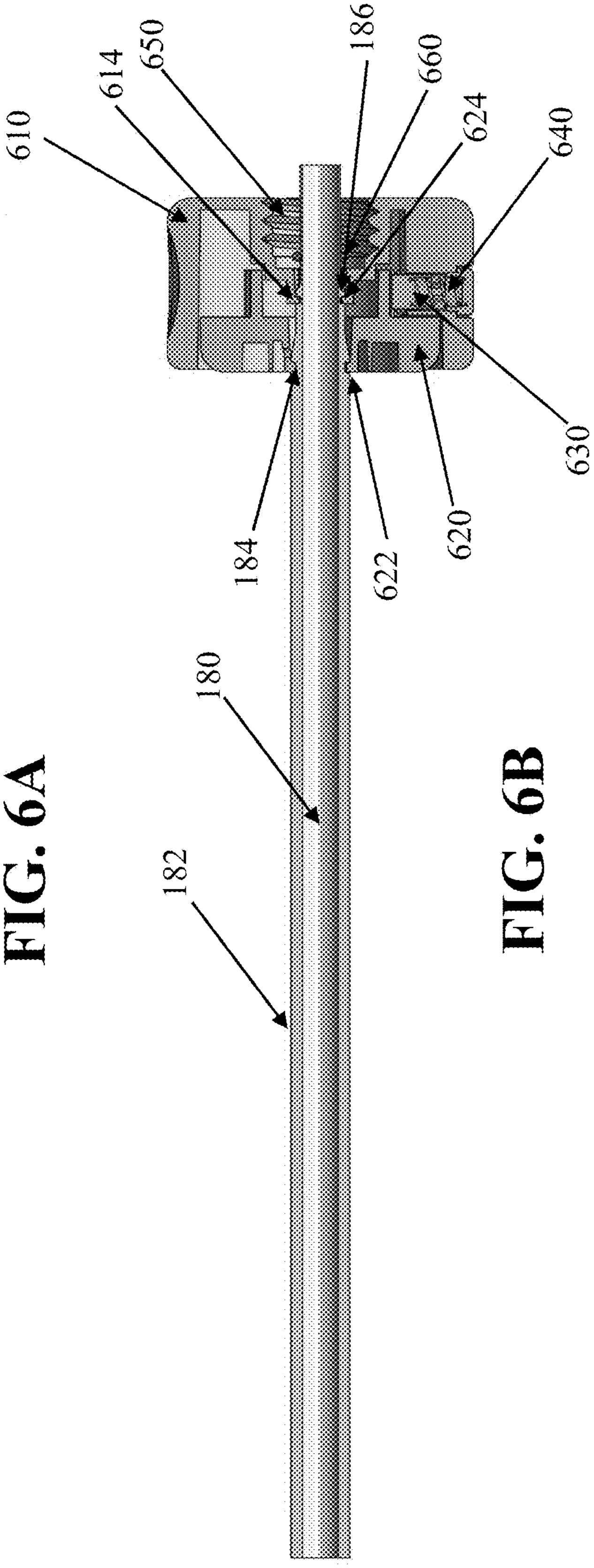

Referring now to FIGS. 1-4, 6A and 6B, the CA mechanism 600 is configured to cause the balloon catheter 300 to rotate relative to the flexible catheter 200 so as to properly orient the medical device at a treatment site. The CA mechanism 600 includes an alignment knob 610, an inner cap 620, a gear tooth 630, and a biasing spring 640. The alignment knob 610 can optionally include divots 612, ribs, rough surface to facilitate in the gripping and/or rotating of the alignment knob 620. The gear tooth 630 is biased into engagement with the inner cap 620 by biasing spring 640. As can be appreciated, other biasing arrangements can be used. The end of the gear tooth engages engagement flanges 622 on the inner cap 620 that engage the outer surface of a hypotube sleeve 182. The engagement flanges 622 are configured to flex into engagement with outer surface of the hypotube sleeve 182 to facilitate in the gripping of the hypotube sleeve 182 with the inner cap 620. The gear tooth 630 also facilitates in the engagement between the alignment knob 610 and the inner knob 620. As such, when the alignment knob is rotated about the longitudinal axis of the housing, the gear tooth 630 can be configured to facilitate in in the rotation of the inner knob and the hypotube sleeve 182 about the longitudinal axis of the housing. As illustrated in FIGS. 6A and 6B, the ends of the engagement flanges 622 can optionally be inserted into a distal groove 184 in the threaded shaft to facilitate in the connection to the hypotube sleeve 182. Also, the alignment knob 610 can optionally include an engagement flange 614 that engages a proximal groove 186 in the threaded shaft to facilitate in the connection to the hypotube sleeve 182. The hypotube sleeve 182 is configured to receive a portion of the hypotube 180. The connection between the hypotube sleeve 182 and the hypotube 180 can be a friction connection, adhesive connection, etc. so that when the hypotube sleeve 182 moves longitudinally and/or rotates about the longitudinal axis of the housing, the hypotube 180 also similarly moves.

The alignment knob 610 is coupled to the hypotube sleeve 182. The alignment knob 610 is rotatable (either clockwise or counterclockwise) around the gear 630 to control the rotational movement of the balloon catheter shaft 310 relative to the flexible catheter 200. The rotation of the alignment knob 610 correspondingly rotates the axial position threaded shaft 520. Rotation of the alignment knob 610 causes rotation of the hypotube sleeve 182, which in turn causes rotation of the hypotube 180, which in turn causes rotation of the balloon catheter 300 relative to the flexible catheter 200. When the medical device on the balloon catheter 300 is a TAV, the alignment knob 601 can be used to rotates the crimped TAV on the balloon catheter 300, thereby controlling the rotational orientation of the TAV leaflet attachment points (commissure) relative to the native anatomical features prior to the expansion of the TAV in the heart. The alignment knob 610 can be rotated to control the rotation movement of the balloon catheter 300 regardless of the locked or unlocked position of the longitudinal adjustment mechanism 500.

The proximal end of the alignment knob 610 can includes a threaded luer connection 650 that is configured to connect to a luer tree 190. A sealing ring 660 can be used to form a liquid seal between the luer tree 190 and the alignment knob 610. The luer tree 190 includes a flexible catheter flush port 192, a guidewire lumen 194 that is configured to receive a guidewire, and a balloon inflation port 196.

Still referring to FIGS. 1-4, the housing 110 further includes a mid-ring 170, and a hemostasis O-ring 175. The mid-ring 170 is contained within the housing 110 and is configured to maintain the alignment of the hypotube sleeve 182 in the housing 110. The hypotube 180 is contained within the body cavity 150 and is configured to allow flush fluid to flow over the balloon catheter shaft 310 and into the flexible catheter 200 as the prosthetic valve is moved and/or expanded at the treatment site. The hypotube 180 is free to translate linearly and rotationally relative to the body cavity 150 as the axial position threaded shaft 520 is correspondingly translated linearly (via the longitudinal adjustment mechanism 500) and/or rotationally (via the CA mechanism 600). The hemostasis O-ring 175 creates a sliding hemostatic seal between the inner surface of the body cavity 150 and an outer surface of the hypotube 180.

As illustrated in FIG. 3, the interior cavity 153 of the body core 152 can have differing inner diameters or cross-sectional areas along the longitudinal length of the body core. The proximal region of the body core is illustrated as having inner cavity that has a larger inner diameter or cross-sectional area that the inner cavity at the distal region of the body core. The larger inner diameter or cross-sectional area that the inner cavity at the proximal region of the body core is shaped and sized to accommodate the hypotube sleeve 182 so that the hypotube sleeve 182 can move longitudinally within the inner cavity at the proximal region of the body core. The small inner diameter or cross-sectional area that the inner cavity at the distal region of the body core can function as a stop or distance limiter to limit or prevent the hypotube sleeve 182 from moving further longitudinally toward the distal end of the housing.

Still referring to FIGS. 1-4, the housing 110 further includes a nose cap 160 attached to the body cavity 150 about the distal end 120*b*. The nose cap 160 is configured to hold the knob 410 and the knob body 420 in place relative to the delivery handle arrangement 100. The nose cap optionally has a size indicator on the outer surface of the nose cap that can optionally provide size information about the flexible catheter or catheter and/or provide size information about the medical device on the flexible catheter or balloon catheter.

Referring now to FIGS. 7A-7D, there is illustrated an exemplary, non-limiting embolic capture filter membrane sock or similar filter 700 that is configured for optional use with a non-limiting flexible catheter 200 and a non-limiting balloon catheter 300.

With reference to FIGS. 7A-7D, there is provided an embolic capture filter membrane sock or similar filter 700 that is mounted on the exterior of a balloon catheter shaft. Balloon catheter 300 is contained within the balloon catheter shaft and includes an inflatable balloon 730. The balloon catheter shaft extends coaxially within a flexible catheter 740 and a flexible catheter shaft 750. The balloon catheter 300 optionally includes a nose 760 that is configured to facilitate movement through arteries or similar conduits. The nose 760 can be formed a soft flexible material that facilitates in the movement of the nose 760 through a vascular system. The nose 760 can optionally be tapered.

Still referring to FIGS. 7A-7D, the embolic capture filter membrane sock 700 includes a porous membrane having one or more pores that are sized to effectively block passage of embolic particles (e.g., 50 μm) and include sufficient hole density to provide minimal resistance to flow when deployed in the aorta (e.g., 20-60% open area vs. remaining material). When the balloon catheter 300 is moved forwarded relative to the flexible catheter 200 prior to inflation of the balloon 730, the embolic capture filter membrane sock 700, when used, expands and contacts the inner lumen of the aorta or surround tissue at a location that is proximal to the balloon 730. When the balloon catheter 300 is retracted relative to the flexible catheter 200, the embolic capture filter membrane sock 700 closes, thereby containing any trapped emboli. The embolic capture filter membrane sock 700 is opened prior to or during inflation of balloon 730 to expand the medical device at the treatment site and is then closed prior to or during deflation of the balloon 730.

Figure 7A:
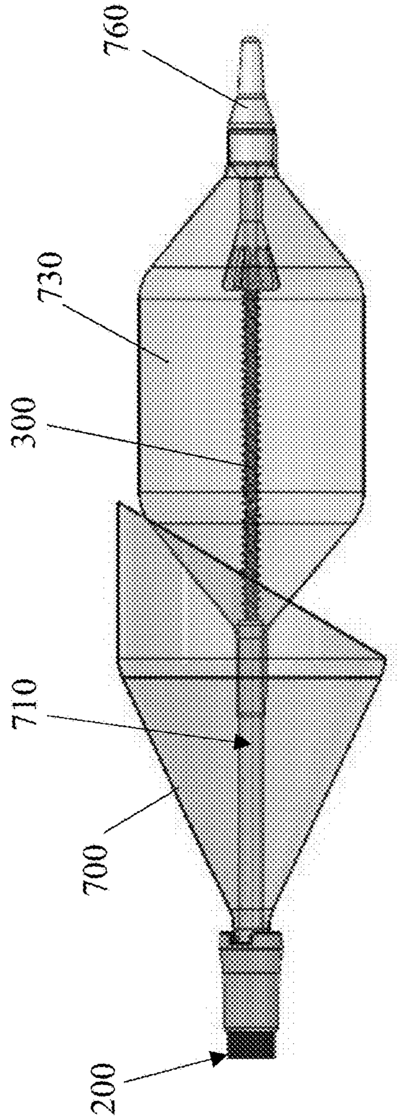
FIGS. 7A-7D depict an exemplary, non-limiting embolic capture filter membrane sock configured for use with a non-limiting flexible catheter and a non-limiting balloon catheter.
Figure 7B:
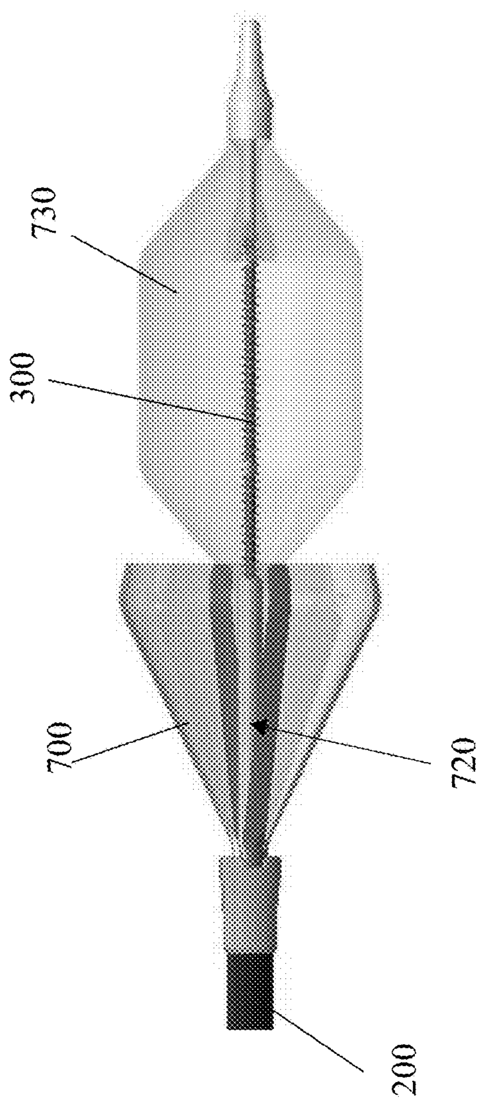
Figure 7D:
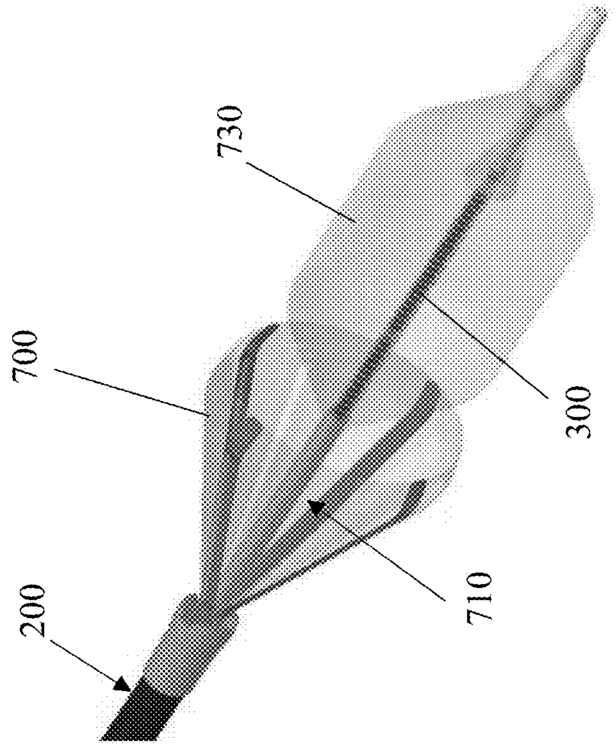
Figure 7C:
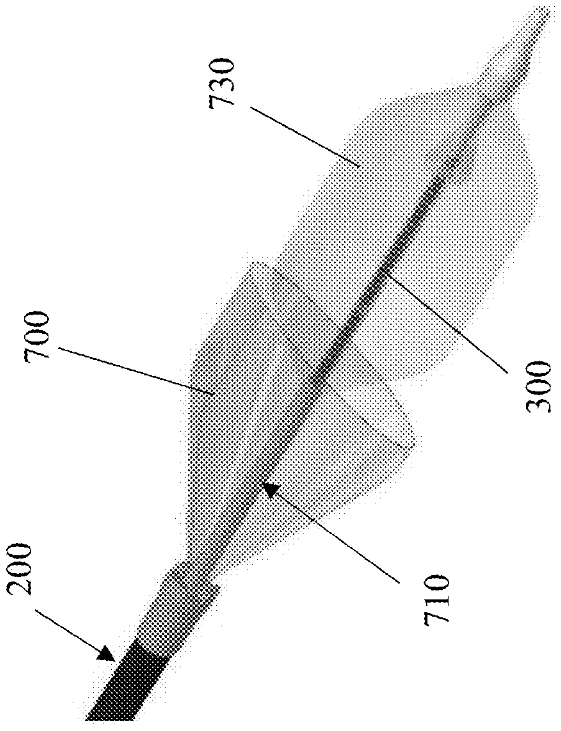
Figure 7E:
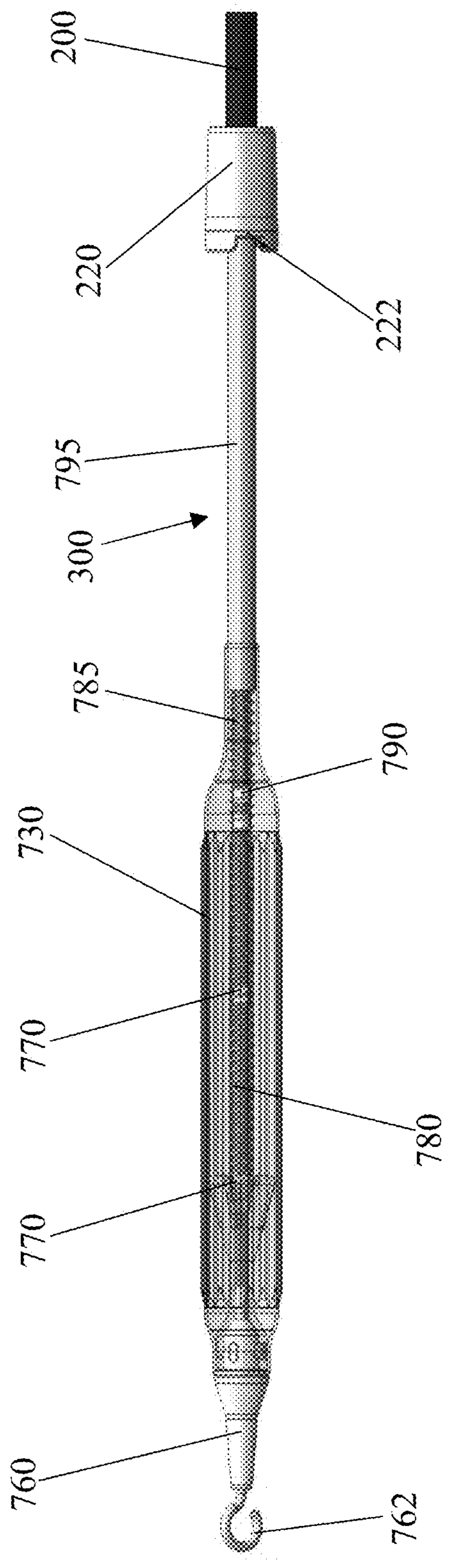
FIG. 7E illustrates the distal region of the flexible catheter and balloon catheter.

Referring now to FIG. 7E, the distal region of the flexible catheter 200 and balloon catheter is illustrated. The distal end of the flexible catheter can includes a collet 220 that optionally includes one or more commissural slots 222. The optional commissural slots 222 can be used to engage a portion of a medical device (e.g., frame of a medical device, etc.) to releasably hold the medical device in place during the positioning of the medical device at a treatment site. The collet 220, when used, can be formed of a rigid material and can optionally be sized to receive a portion of filter 700, when used. Optionally markers 770 can be included on the distal region of the balloon catheter 310 to function as positioning indicators during the positioning of the medical device at a treatment site. An inflation spring 780 can optionally be used to facilitate in the inflation of the inflatable balloon 730. A hypotube 790 can optionally be used to reinforce the guide shaft 785 of the balloon catheter 300. The hypotube 790, when used, can be configured to encircle a portion of the guide shaft 785. The hypotube 790, when used, can be flexible or rigid. The hypotube 790, when used, can be formed of a metal or plastic material; however, other materials can be used. A distal portion of the guide shaft 785 can optionally be covered by a reinforcement layer or shaft 795 (e.g., a braided shaft, etc.) to provide reinforcement to a portion of the guide shaft 785 that extends outwardly from the distal end of the flexible catheter 200 (e.g., reinforcement layer or shaft provides kink resistance to a portion of the guide shaft, etc.). The material used to form the reinforcement layer or shaft 795 is non-limiting (e.g., metal, plastic, etc.). Generally, the reinforcement layer or shaft 795, when used, extends 0.1-40% (and all values and ranges therebetween the longitudinal length of the guide shaft 785. Generally, the reinforcement layer or shaft 795, when used, is positioned rearwardly of the inflatable balloon 730 on the balloon catheter 200 or 0.01-5% (and all values and ranges therebetween) of the longitudinal axis of the inflatable balloon 730 is connected to an outer surface of the reinforcement layer or shaft 795. In one non-limiting configuration, a proximal end of the guide shaft 785 is connected to the distal end of hypotube 180 in the delivery handle, and the distal end or distal region of the guide shaft extends through the distal end of the inflatable balloon 730 and is connected to the optionally nose 760. As illustrated in FIG. 7E, the end of the nose 760 can optionally include a removable hook 762 that is configured to function as a hanging feature of the distal end of the balloon catheter prior to use of the balloon catheter. The optional removable hook 762 is configured to be removed form the nose 730 prior to the balloon catheter being inserted into a vascular system.

Figure 8:
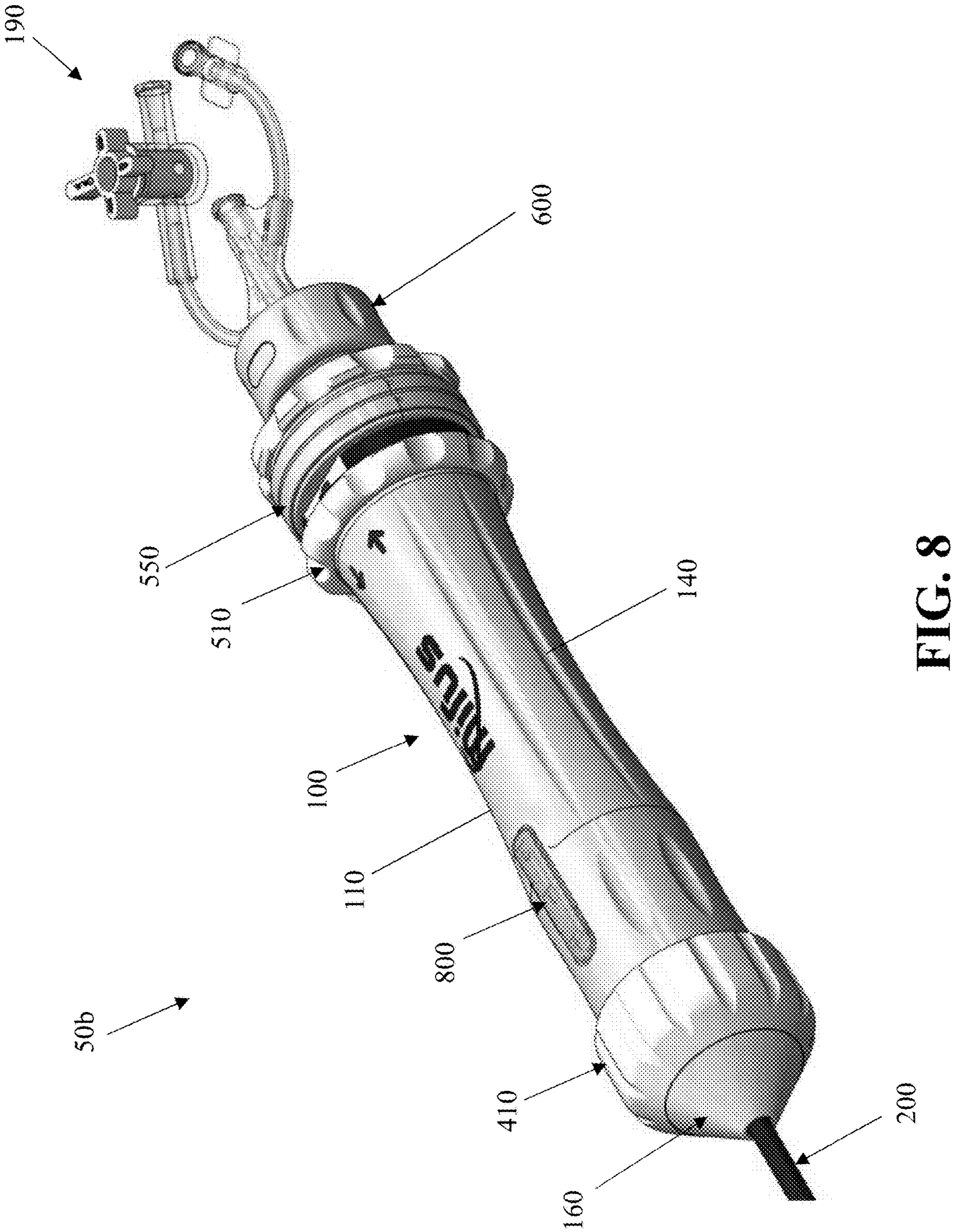
FIG. 8 depicts another exemplary, non-limiting delivery system comprising another non-limiting handle arrangement in accordance with the present disclosure.
Figure 9:
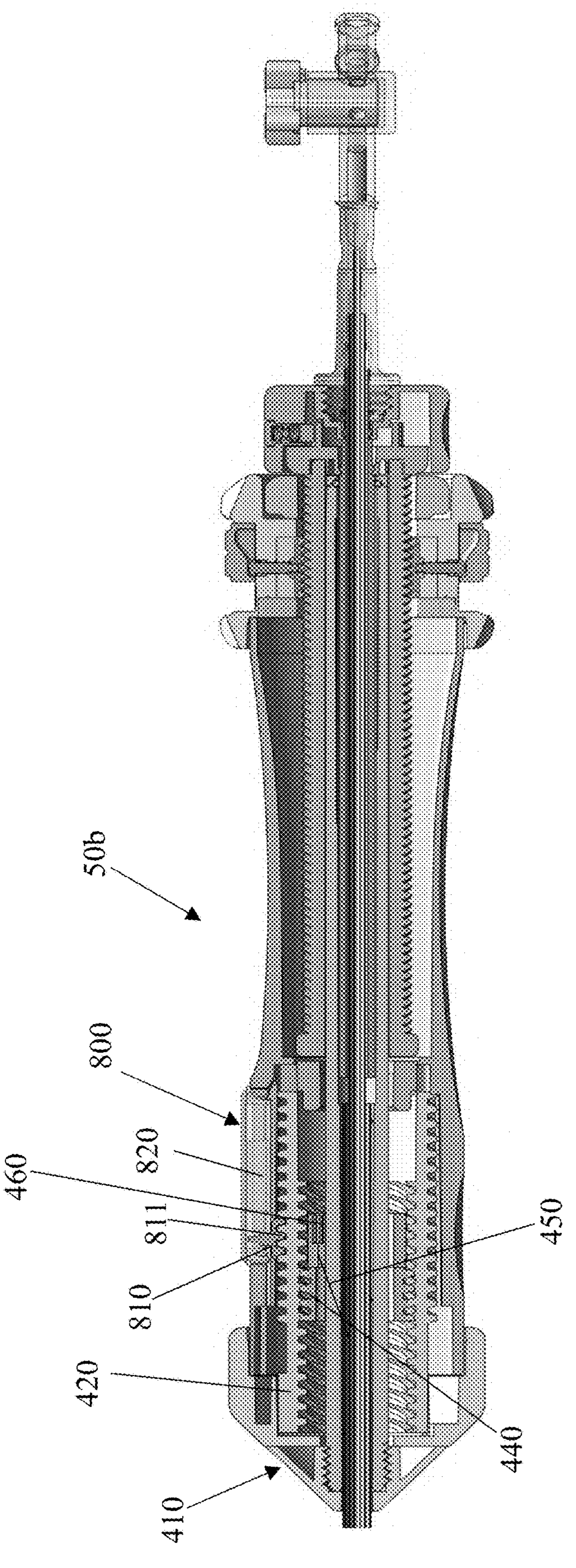
FIG. 9 is a cross-sectional side view of the delivery handle arrangement of FIG. 8.

Referring now to FIGS. 8 and 9, an optional modification of the delivery system 50*b* of FIGS. 1-4 is illustrated. The components of the delivery system 50*b* of FIGS. 1-4 are generally the same as the delivery system 50*b* of FIGS. 8 and 9, thus such similar components and operation of the components will not be repeated herein. The new modifications of the delivery system 50*b* of FIGS. 8 and 9 include the handle 100 has a flex indicator 800 that is configured to provide to a user information on the degree or amount of flex or bend present in the distal region of the flexible catheter 200. The flex indicator 800 includes a needle 810 and a protector 820. The needle 810 includes one or more threads 811 that are configured to engage threading on the knob body 420. As the knob 410 is rotated (either clockwise or counterclockwise), the needle 810 translates along the knob body 420, indicating the degree or amount of flex present in the distal region of flexible catheter 200. The protector 820 can be a clear plastic or glass material that enables a user to see the needle 810. As can be appreciated, multiple flex indicators 800 can be used (e.g., flex indicators located on both sides of the housing, etc.). As can also be appreciated, other types of indicators can be used (e.g., electronic indicator, etc.). The flex indicator 800 can include reference numbers and/or images to provide additional information to a user regarding the degree or amount of flex present in the distal region of flexible catheter 200. The flex indicator 800 is illustrated as being located at the distal region of the housing; however, this is not required.

As illustrated in FIG. 8, a MiRus logo can optionally be located on the housing 110. Such a logo or other type of marking can be positioned on the housing to function as an indicator to the user for proper holding and/or positioning (e.g., commissural alignment, etc.) of the handle 110 during operation of the handle 100. As can be appreciated, the flex indicator 800 can also be positioned on the housing to function as an indicator to the user for proper holding and/or positioning (e.g., commissural alignment, etc.) of the handle 110 during operation of the handle 100.

A further optional modification to the delivery system 50*a* is that control knob 610 is optionally not connected to shaft 520. In such a non-limiting arrangement, control knob 610 can be moved away from a proximal end of the shaft 520; however, this is not required.

Figure 10:
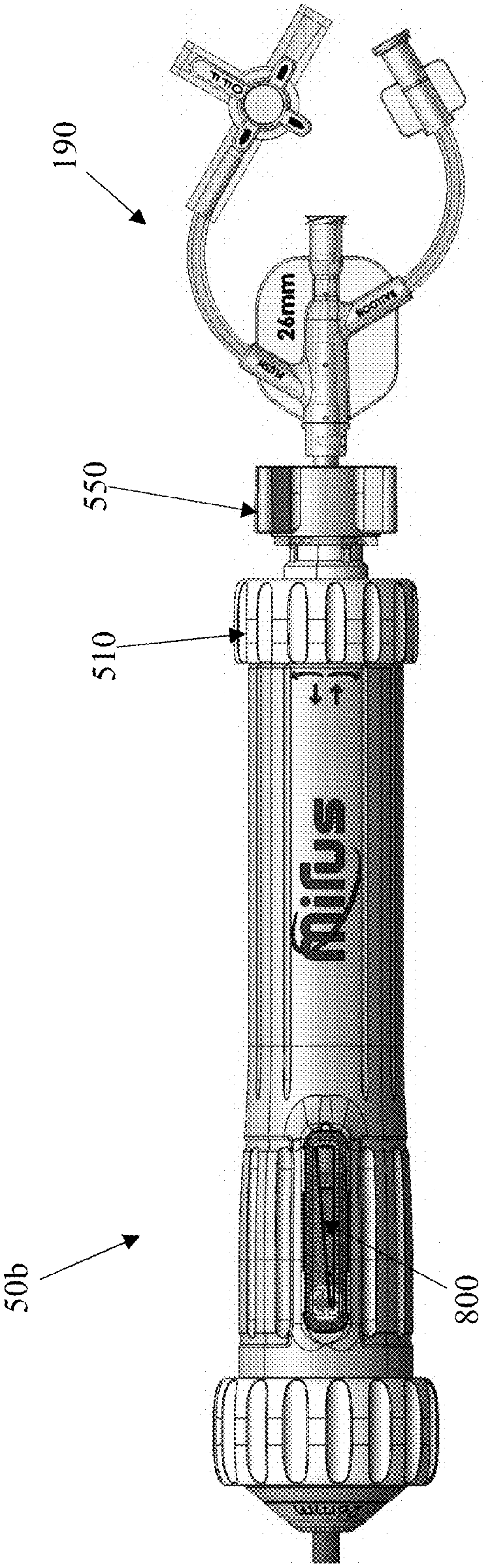
FIG. 10 depicts another exemplary, non-limiting delivery system comprising another non-limiting handle arrangement in accordance with the present disclosure.
Figure 11:
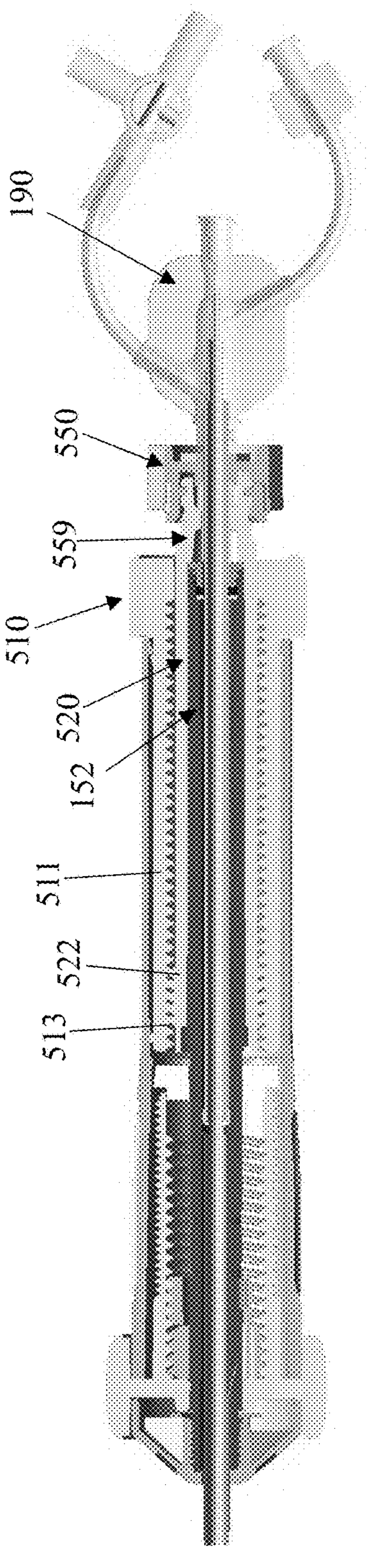
FIG. 11 is a cross-sectional side view of the delivery handle arrangement of FIG. 10.
Figure 12:
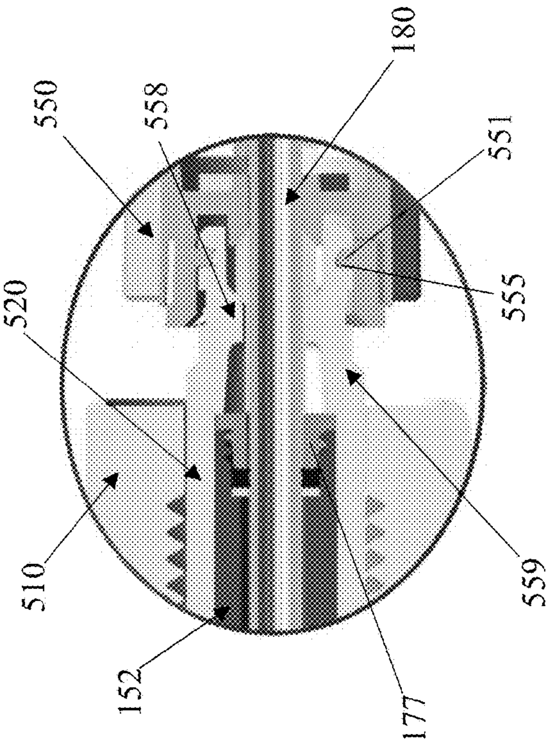
FIG. 12 is an enlarged view of the longitudinal adjustment mechanism of FIGS. 10 and 11.

Referring now to FIGS. 10-12, another exemplary, non-limiting delivery system 50*a* is illustrated. The components of the delivery system 50*b* of FIGS. 1-4, 8 and 9 are generally the same as the delivery system 50*b* of FIGS. 10-12, thus such similar components and operation of the components will not be repeated herein. The delivery system 50*a* illustrated in FIGS. 10-12 includes a modified switch 550 and a modified body core 152. Unlike the switch 550 being positioned and is movable between the first stop region 512 and the second stop region 514 of the control knob 510 as illustrated in FIGS. 1-4, 8 and 9, switch 550 is a rotational switch that rotated about the longitudinal axis of the housing 110. The first stop region 512 and the second stop region 514 of the control knob 510 are also eliminated. Also, the body core 152 is absent a large flange 154 as illustrated in FIGS. 2-4 and 9, and a proximal portion is control knob 510 is not positioned about flange 154.

As illustrated in FIGS. 11-12, switch 550 is rotatably positioned on flange 559 of the threaded shaft 520. The flange 559 can includes a rotation slot 555 to receive a rotation rib 551 on switch 550 and these features are configured to enable the switch to rotate on the flange 559 between the locked and uplocked positions; however, other configurations can be used. The switch 550 includes a cavity that the hypotube 180 can pass through.

To engage fine longitudinal positioning of the hypotube 180, the switch 550 is turned on the flange 559 of the threaded shaft 520 to the locked position. In the locked position, a collet 558 on the flange portion 559 is compressed on the hypotube 180 thereby preventing rapid longitudinal movement of the hypotube 180. When the switch 550 is in the locked position, the turning of the control knob 510 causes the collet 558 to be moved to its compressed position, which in turn precents allows the hypotube 180 from being freely longitudinally moved in the housing and past the collet 184. As such, when the switch 550 is in the locked position, the hypotube 180 can thus be longitudinally move by a user rotating control knob 510. Rotation of the control knob 510 causes the threaded region 513 of the body 511 of the control knob 510, that is located in the housing, to engage a threaded region 522 on the body of the threaded shaft 520, which thereby causes longitudinal movement of the threaded shaft 520 relative to the housing 110. The movement of the threaded shaft 520 causes movement of hypotube 180 that is releasably engaged with compressed collet 558 on the flange portion 559 of the threaded shaft 520.

When the switch 550 is in the unlocked position, the collet 558 releases from the hypotube 180 thereby allowing the hypotube 180 to freely slide forwards or backwards along the longitudinal axis of the housing. The control knob 180 can be rotated when the switch 550 is located in both the locked and unlocked position. The rotation of the control knob 180 will cause longitudinal movement of the threaded shaft 520; however, since the collet 558 is not engaged with the hypotube 180, movement of the threaded shaft 520 will not result in the movement of the hypotube 180. The hypotube 180 can be longitudinally moved by grasping the luer tree 190 and moving the luer tree along the longitudinal axis of the housing, which in turn will result in the movement of the hypotube 180 along the longitudinal axis of the housing.

The delivery system 50*a* illustrated in FIGS. 10-12 also does not have a separate commissural alignment knob. The delivery system 50*a* illustrated in FIGS. 1-4, 8 and 9 has an alignment knob 610. The delivery system 50*a* illustrated in FIGS. 10-12 is absent an alignment knob 610. The luer tree 190, instead of the alignment knob 610, is used by the user to rotate the hypotube about the longitudinal axis of the housing for commissural alignment of the medical device at the treatment site. When the switch 550 is in the locked position, the luer tree 190 is prevented from rotating the hypotube due to the collet 558 being compressed against the hypotube 180. When the switch 550 is in the unlocked position, the hypotube 180 can be freely rotated about the longitudinal axis of the housing due to the collet 558 being in the non-compressed position. In the embodiments of the delivery system 50*a* illustrated in FIGS. 1-4, 8 and 9, the alignment knob 610 can be rotated when the switch is in both the locked and unlocked position; however, this is not required.

As illustrated in FIGS. 11 and 12, the proximal end of the body core 152 can optionally include an O-ring 177 to create a liquid seal between the hypotube 180 and the body core 152.

It should be understood, however, that all of these and similar terms are to be associated with the appropriate physical quantities and are merely convenient labels applied to these quantities.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. These and other modifications of the preferred embodiments as well as other embodiments of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

The description of embodiments and examples has been presented for purposes of illustration and description. It is not intended to be exhaustive or limiting to the forms described. Numerous modifications are possible in light of the teachings herein. Some of those modifications have been discussed, and others will be understood by those skilled in the art. The embodiments were chosen and described in order to illustrate principles of various embodiments as are suited to particular uses contemplated. The scope is, of course, not limited to the examples set forth herein, but can be employed in any number of applications and equivalent devices by those of ordinary skill in the art.

To aid the Patent Office and any readers of this application and any resulting patent in interpreting the claims appended hereto, applicants do not intend any of the appended claims or claim elements to invoke 35 U.S.C. 112(f) unless the words “means for” or “step for” are explicitly used in the particular claim.

What is claimed:

1. A delivery handle arrangement that facilitates delivery of a medical device to a treatment site; said delivery handle arrangement comprising:

- a housing having an inner core that at least partially extends linearly between a proximal end and a distal end of said housing; and wherein said inner core at least partially receives a hypotube;
- a flexible catheter and a balloon catheter; a proximal region of said flexible catheter is connected to said housing; said balloon catheter is movable relative to said flexible catheter; a distal region of said hypotube is connected to a proximal region of said balloon catheter;
- a longitudinal adjustment mechanism that is configured to control longitudinal movement of said hypotube; said longitudinal adjustment mechanism includes:
  - a control knob that is movable relative to said housing; and
  - a switch that is configured to move between a lock or unlocked position; and
  - wherein said hypotube is movable linearly within said housing when said longitudinal adjustment mechanism is in said locked position and said control knob is moved; and
  - wherein said hypotube is movable linearly within said housing when said longitudinal adjustment mechanism is in said unlocked position and linear movement of said hypotube in said housing does not require movement of said control knob.

2. The delivery handle arrangement as defined in claim 1, wherein said control knob is rotatable about a longitudinal axis of said housing.

3. The delivery handle arrangement as defined in claim 1, wherein said control knob includes a first stop region and a second stop region that are spaced from one another; said switch is positioned between said first stop region and said second stop region.

4. The delivery handle arrangement as defined in claim 1, wherein said longitudinal adjustment mechanism further includes a movable catch, a threaded insert and an insert biasing arrangement; said switch includes a channel having a first stop and a second stop; said first stop has a larger width than said second stop; said catch is positioned at said first stop when said switch is moved to said unlocked position; said catch positioned at said second stop when said switch moves to said locked position; said biasing arrangement is configured to bias said catch upwardly in said channel at said first stop when said switch is moved to said unlocked position; said channel is configured to cause said catch to move downwardly when said switch is moved from said unlocked position to said locked position; said downward movement of said switch is configured to cause said threaded insert to move downwardly and engage a threaded shaft; said threaded shaft is connected to said hypotube.

5. The delivery handle arrangement as defined in claim 4, wherein rotation of said control knob in a first direction causes said shaft to move linearly from or near said proximal end towards said distal end within said housing when said switch is in said locked position; wherein rotation of said control knob in a second opposite direction causes said shaft to move linearly from or near said distal end towards said proximal end when said switch is in said locked position; and wherein rotation of said control knob does not cause said shaft to move linearly between said distal end and proximal end when said switch is in said unlocked position.

6. The delivery handle arrangement as defined in claim 1, wherein said longitudinal adjustment mechanism further includes a fine alignment sleeve; said control knob includes a threaded body positioned in said housing; said fine alignment sleeve is positioned in said housing and movable along a longitudinal axis of said housing; said fine alignment sleeve includes a threaded region that threadedly engages said threaded body; said control knob is configured to move said fine alignment sleeve along said longitudinal axis of said housing when said control knob is rotated; said longitudinal axis of said housing includes a compression flange that is configured to releasably engage and disengage from said hypotube or sleeve on said hypotube; said switch in said locked position causes said compression flange to releasably engage said hypotube or sleeve on said hypotube; said switch in said unlocked position causes said compression flange to disengage said hypotube or sleeve on said hypotube.

7. The delivery handle arrangement as defined in claim 6, wherein rotation of said control knob in a first direction causes said fine alignment sleeve to move linearly from or near said proximal end towards said distal end within said housing when said switch is in said locked position; wherein rotation of said control knob in a second opposite direction causes said fine alignment sleeve to move linearly from or near said distal end towards said proximal end when said switch is in said locked position; and wherein rotation of said control causes said fine alignment sleeve to move linearly between said distal end and proximal end when said switch is in said unlocked position and does not cause said hypotube to move linearly between said distal end and proximal end.

8. The delivery handle arrangement as defined in claim 1, further comprising a flex adjustment mechanism that is configured to controllably bend or flex a distal region of said flexible catheter; said flex mechanism includes:

- a flex knob that is movably connected to said housing; said flex knob includes a body portion that is at least partially positioned in said inner core of said housing;
- a flex insert that is at least partially positioned in said housing; said flex insert is in engagement with said body portion; said flex insert is caused to move by movement of said flex knob;
- an actuation insert that is at least partially positioned in said housing; said actuation insert is in engagement with said body portion of said flex knob and/or said flex inert; said actuation insert is caused to move by movement of said flex knob and/or said flex insert; and
- a wire member; said wire member is coupled at a proximal end to said flex insert and/or said actuation insert and at a distal end to a distal region of said flexible catheter; and
- wherein said distal region of said flexible catheter is caused to controllably bend during movement of said flex knob.

9. The delivery handle arrangement as defined in claim 8, wherein said flex knob is configured to rotate on said housing; said flex knob is configured to cause a portion of said wire member to be drawn into said housing when rotated in a first direction, and wherein said distal region of said flexible catheter is caused to bend when said flex knob is rotated in said first direction; said flex knob is configured to cause said wire member to be moved outwardly from said housing when rotated in a second direction, and wherein said distal region of said flexible catheter is caused to unbend when said flex knob is rotated in said second direction.

10. The delivery handle arrangement as defined in claim 9, wherein said first flex indicator includes a movable needle and a flex bend graphic; and wherein said needle translates along said housing and along a portion of said flex bend graphic to indicate to a user a degree of bending of said distal region of said flexible catheter.

11. The delivery handle arrangement as defined in claim 9, wherein said first flex indicator is located rearwardly of said flex knob.

12. The delivery handle arrangement as defined in claim 8, further including a first flex indicator arrangement located on said housing; said first flex indicator arrangement includes a first flex indicator that is configured to provide information to a user about a degree or amount of bending of said distal portion of said flexible catheter prior, during and/or after said flex knob is rotated.

13. The delivery handle arrangement as defined in claim 12, wherein said first flex indicator arrangement includes a flex indicator window on an outer surface of said housing and wherein said a first flex indicator is covered by said flex indicator window.

14. The delivery arrangement as defined in claim 13, further including a second flex indicator arrangement; said second flex indicator arrangement includes a second flex indicator; said second flex indicator is positioned on an opposite side of said housing from said first flex indicator.

15. The delivery handle arrangement as defined in claim 8, wherein said flex knob does not move along a longitudinal axis of said housing wherein said flex knob is moved on said housing.

16. The delivery handle arrangement as defined in claim 8 wherein said distal end of said flexible catheter includes a pull ring; said wire member is connected to said pull ring; said pull ring is spaced from a distal end of said flexible catheter.

17. The delivery handle arrangement as defined in claim 16, wherein said distal portion of said flexible catheter includes a flexible hypotube or spring; said flexible hypotube or spring is configured to a) bend when said distal portion of said flexible catheter is caused to bend by said guide flex arrangement, and b) cause said distal portion of said flexible catheter to unbend when said guide flex arrangement allows said distal portion of said flexible catheter to unbend from a bent position said flexible hypotube or spring is positioned further from said distal end of said flexible catheter than said pull ring.

18. The delivery handle arrangement as defined in claim 17, wherein said distal portion of said flexible catheter includes said flexible hypotube; said flexible hypotube is a laser cut hypotube.

19. The delivery handle arrangement as defined in claim 1, further comprising a rotational mechanism that is configured to rotate said balloon catheter relative to said flexible catheter; said rotational mechanism includes an alignment component that engages said hypotube: rotation of said alignment component about a longitudinal axis of said housing is configured to cause said hypotube to rotate about said longitudinal axis of said housing; and wherein rotation of said hypotube causes said balloon catheter to rotate within said flexible catheter.

20. The delivery handle arrangement as defined in claim 19, wherein said alignment mechanism is configured to advance a distal end of said hypotube toward and away from said distal end of said housing.

21. The delivery handle arrangement as defined in claim 19, wherein said alignment component is an alignment knob arrangement that includes an alignment knob, an inner cap, a gear tooth, and a biasing arrangement; said gear tooth is biased into engagement with the inner cap by said biasing arrangement; an end of said the gear tooth is configured to engage flexible engagement flanges on said inner cap to cause said flexible engagement flanges to engage an outer surface of said hypotube or sleeve about said hypotube.

22. The delivery handle arrangement as defined in claim 19, wherein said alignment mechanism is configured to advance a distal end of said hypotube toward and away from said distal end of said housing only when said switch is in said unlocked position; said alignment mechanism is configured to rotate said hypotube when said switch is in either said locked or unlocked position.

23. The delivery handle arrangement as defined in claim 19, wherein said alignment component is a luer tree that is connected to said hypotube.

24. The delivery handle arrangement as defined in claim 23, wherein said alignment mechanism is configured to advance a distal end of said hypotube toward and away from said distal end of said housing only when said switch is in said unlocked position; said alignment mechanism is configured to only rotate said hypotube when said switch is in said unlocked position.

25. The delivery handle arrangement as defined in claim 1, further comprising a luer tree; said luer tree includes one or more of a flush port, a guidewire lumen that is configured to receive a guidewire, and/or a balloon inflation port.

26. The delivery handle arrangement as defined in claim 1, wherein said hypotube is configured to allow flush fluid to flow at least partially over said balloon catheter and at least partially into said flexible catheter; and wherein a sealing arrangement is configured to creates a sliding hemostatic seal between outer surface of said hypotube and one or more components in said housing.

27. The delivery handle arrangement as defined in claim 1, wherein said medical device is a prosthetic valve.

28. A delivery handle arrangement that facilitates delivery of a medical device to a treatment site; said delivery handle arrangement comprising:

a housing having an inner core that extends linearly between a proximal end and a distal end of said housing; said inner core at least partially receives a hypotube;

a flexible catheter and a balloon catheter; a proximal region of said flexible catheter is connected to said housing; said balloon catheter is movable relative to said flexible catheter; a distal region of said hypotube is connected to a proximal region of said balloon catheter;

a longitudinal adjustment mechanism that is configured to control longitudinal movement of said hypotube; said longitudinal adjustment mechanism includes:

a control knob that is rotatable about a longitudinal axis of said housing; said control knob includes a first stop region and a second stop region that are spaced from one another; and a switch that is configured to move between a lock or unlocked position; said switch is positioned between said first stop region and said second stop region of said control knob; and wherein said hypotube is movable linearly within said housing when said longitudinal adjustment mechanism is in said locked position and said control knob is moved; and wherein said hypotube is movable linearly within said housing when said longitudinal adjustment mechanism is in said unlocked position and linear movement of said hypotube in said housing does not require movement of said control knob.

29. The delivery handle arrangement as defined in claim 28, wherein said longitudinal adjustment mechanism further includes a movable catch, a threaded insert and an insert biasing arrangement; said switch includes a channel having a first stop and a second stop; said first stop has a larger width than said second stop; said catch is positioned at said first stop when said switch is moved to said unlocked position; said catch positioned at said second stop when said switch moves to said locked position; said biasing arrangement is configured to bias said catch upwardly in said channel at said first stop when said switch is moved to said unlocked position; said channel is configured to cause said catch to move downwardly when said switch is moved from said unlocked position to said locked position; said downward movement of said switch is configured to cause said threaded insert to move downwardly and engage a threaded shaft; said threaded shaft is connected to said hypotube; and wherein rotation of said control knob in a first direction causes said shaft to move linearly from or near said proximal end towards said distal end within said housing when said switch is in said locked position; wherein rotation of said control knob in a second opposite direction causes said shaft to move linearly from or near said distal end towards said proximal end when said switch is in said locked position; and wherein rotation of said control knob does not cause said shaft to move linearly between said distal end and proximal end when said switch is in said unlocked position.

30. The delivery handle arrangement as defined in claim 29, wherein said longitudinal adjustment mechanism further includes a fine alignment sleeve; said control knob includes a threaded body positioned in said housing; said fine alignment sleeve is positioned in said housing and is movable along a longitudinal axis of said housing; said fine alignment sleeve includes a threaded region that threadedly engages said threaded body; said control knob is configured to move said fine alignment sleeve along said longitudinal axis of said housing when said control knob is rotated; said longitudinal axis of said housing includes a compression flange that is configured to releasably engage and disengage from said hypotube or sleeve on said hypotube; said switch in said locked position causes said compression flange to releasably engage said hypotube or sleeve on said hypotube; said switch in said unlocked position causes said compression flange to disengage said hypotube or sleeve on said hypotube; and wherein rotation of said control knob in a first direction causes said fine alignment sleeve to move linearly from or near said proximal end towards said distal end within said housing when said switch is in said locked position; wherein rotation of said control knob in a second opposite direction causes said fine alignment sleeve to move linearly from or near said distal end towards said proximal end when said switch is in said locked position; and wherein rotation of said control causes said fine alignment sleeve to move linearly between said distal end and proximal end when said switch is in said unlocked position and does not cause said hypotube to move linearly between said distal end and proximal end.

31. The delivery handle arrangement as defined in claim 30, further comprising a flex adjustment mechanism that is configured to controllably bend or flex a distal region of said flexible catheter; said flex mechanism includes:

a flex knob that is movably connected to said housing; said flex knob includes a body portion that is at least partially positioned in said inner core of said housing; said flex knob is configured to rotate on said housing; said flex knob does not move along a longitudinal axis of said housing wherein said flex knob is moved on said housing;

a flex insert that is at least partially positioned in said housing; said flex insert is in engagement with said body portion; said flex insert is caused to move by movement of said flex knob;

an actuation insert that is at least partially positioned in said housing; said actuation insert is in engagement with said body portion of said flex knob and/or said flex inert; said actuation insert is caused to move by movement of said flex knob and/or said flex insert; and a wire member; said wire member is coupled at a proximal end to said flex insert and/or said actuation insert and at a distal end to a distal region of said flexible catheter; and wherein said distal region of said flexible catheter is caused to controllably bend during movement of said flex knob; and wherein said flex knob is configured to cause a portion of said wire member to be drawn into said housing when rotated in a first direction, and wherein said distal region of said flexible catheter is caused to bend when said flex knob is rotated in said first direction; and wherein said flex knob is configured to cause said wire member to be moved outwardly from said housing when rotated in a second direction, and wherein said distal region of said flexible catheter is caused to unbend when said flex knob is rotated in said second direction.

32. The delivery handle arrangement as defined in claim 31, further including a first flex indicator arrangement located on said housing; said first flex indicator arrangement includes a first flex indicator that is configured to provide information to a user about a degree or amount of bending of said distal portion of said flexible catheter prior, during and/or after said flex knob is rotated; said first flex indicator arrangement includes a flex indicator window on an outer surface of said housing and wherein said a first flex indicator is covered by said flex indicator window; said first flex indicator is located rearwardly of said flex knob; said first flex indicator includes a movable needle and a flex bend graphic; and wherein said needle translates along said housing and along a portion of said flex bend graphic to indicate to a user a degree of bending of said distal region of said flexible catheter.

33. The delivery arrangement as defined in claim 32, further including a second flex indicator arrangement; said second flex indicator arrangement includes a second flex indicator; said second flex indicator is positioned on an opposite side of said housing from said first flex indicator.

34. The delivery handle arrangement as defined in claim 33, wherein said distal end of said flexible catheter includes a pull ring; said wire member is connected to said pull ring; said pull ring is spaced from a distal end of said flexible catheter; said distal portion of said flexible catheter includes a flexible hypotube or spring; said flexible hypotube or spring is configured to a) bend when said distal portion of said flexible catheter is caused to bend by said guide flex arrangement, and b) cause said distal portion of said flexible catheter to unbend when said guide flex arrangement allows said distal portion of said flexible catheter to unbend from a bent position said flexible hypotube or spring is positioned further from said distal end of said flexible catheter than said pull ring.

35. The delivery handle arrangement as defined in claim 28, further comprising a rotational mechanism that is configured to rotate said balloon catheter relative to said flexible catheter; said rotational mechanism includes an alignment component that engages said hypotube: rotation of said alignment component about a longitudinal axis of said housing is configured to cause said hypotube to rotate about said longitudinal axis of said housing; and wherein rotation of said hypotube causes said balloon catheter to rotate within said flexible catheter; said alignment mechanism is configured to advance a distal end of said hypotube toward and away from said distal end of said housing; said alignment component is an alignment knob arrangement that includes an alignment knob, an inner cap, a gear tooth, and a biasing arrangement; said gear tooth is biased into engagement with the inner cap by said biasing arrangement; an end of said the gear tooth is configured to engage flexible engagement flanges on said inner cap to cause said flexible engagement flanges to engage an outer surface of said hypotube or sleeve about said hypotube; said alignment mechanism is configured to advance a distal end of said hypotube toward and away from said distal end of said housing only when said switch is in said unlocked position; said alignment mechanism is configured to rotate said hypotube when said switch is in either said locked or unlocked position; said alignment mechanism is configured to advance a distal end of said hypotube toward and away from said distal end of said housing only when said switch is in said unlocked position; said alignment mechanism is configured to only rotate said hypotube when said switch is in said unlocked position.

36. The delivery handle arrangement as defined in claim 28, wherein said longitudinal adjustment mechanism further includes a fine alignment sleeve; said control knob includes a threaded body positioned in said housing; said fine alignment sleeve is positioned in said housing and is movable along a longitudinal axis of said housing; said fine alignment sleeve includes a threaded region that threadedly engages said threaded body; said control knob is configured to move said fine alignment sleeve along said longitudinal axis of said housing when said control knob is rotated; said longitudinal axis of said housing includes a compression flange that is configured to releasably engage and disengage from said hypotube or sleeve on said hypotube; said switch in said locked position causes said compression flange to releasably engage said hypotube or sleeve on said hypotube; said switch in said unlocked position causes said compression flange to disengage said hypotube or sleeve on said hypotube; and wherein rotation of said control knob in a first direction causes said fine alignment sleeve to move linearly from or near said proximal end towards said distal end within said housing when said switch is in said locked position; wherein rotation of said control knob in a second opposite direction causes said fine alignment sleeve to move linearly from or near said distal end towards said proximal end when said switch is in said locked position; and wherein rotation of said control causes said fine alignment sleeve to move linearly between said distal end and proximal end when said switch is in said unlocked position and does not cause said hypotube to move linearly between said distal end and proximal end.

37. The delivery handle arrangement as defined in claim 28, further comprising a flex adjustment mechanism that is configured to controllably bend or flex a distal region of said flexible catheter; said flex mechanism includes:

a flex knob that is movably connected to said housing; said flex knob includes a body portion that is at least partially positioned in said inner core of said housing; said flex knob is configured to rotate on said housing; said flex knob does not move along a longitudinal axis of said housing wherein said flex knob is moved on said housing;

a flex insert that is at least partially positioned in said housing; said flex insert is in engagement with said body portion; said flex insert is caused to move by movement of said flex knob;

an actuation insert that is at least partially positioned in said housing; said actuation insert is in engagement with said body portion of said flex knob and/or said flex inert; said actuation insert is caused to move by movement of said flex knob and/or said flex insert; and a wire member; said wire member is coupled at a proximal end to said flex insert and/or said actuation insert and at a distal end to a distal region of said flexible catheter; and wherein said distal region of said flexible catheter is caused to controllably bend during movement of said flex knob; and wherein said flex knob is configured to cause a portion of said wire member to be drawn into said housing when rotated in a first direction, and wherein said distal region of said flexible catheter is caused to bend when said flex knob is rotated in said first direction; and wherein said flex knob is configured to cause said wire member to be moved outwardly from said housing when rotated in a second direction, and wherein said distal region of said flexible catheter is caused to unbend when said flex knob is rotated in said second direction.

38. The delivery handle arrangement as defined in claim 37, further including a first flex indicator arrangement located on said housing; said first flex indicator arrangement includes a first flex indicator that is configured to provide information to a user about a degree or amount of bending of said distal portion of said flexible catheter prior, during and/or after said flex knob is rotated; said first flex indicator arrangement includes a flex indicator window on an outer surface of said housing and wherein said a first flex indicator is covered by said flex indicator window; said first flex indicator is located rearwardly of said flex knob; said first flex indicator includes a movable needle and a flex bend graphic; and wherein said needle translates along said housing and along a portion of said flex bend graphic to indicate to a user a degree of bending of said distal region of said flexible catheter.

39. The delivery arrangement as defined in claim 38, further including a second flex indicator arrangement; said second flex indicator arrangement includes a second flex indicator; said second flex indicator is positioned on an opposite side of said housing from said first flex indicator.

40. The delivery handle arrangement as defined in claim 37, wherein said distal end of said flexible catheter includes a pull ring; said wire member is connected to said pull ring; said pull ring is spaced from a distal end of said flexible catheter; said distal portion of said flexible catheter includes a flexible hypotube or spring; said flexible hypotube or spring is configured to a) bend when said distal portion of said flexible catheter is caused to bend by said guide flex arrangement, and b) cause said distal portion of said flexible catheter to unbend when said guide flex arrangement allows said distal portion of said flexible catheter to unbend from a bent position said flexible hypotube or spring is positioned further from said distal end of said flexible catheter than said pull ring.

41. The delivery handle arrangement as defined in claim 34, further comprising a rotational mechanism that is configured to rotate said balloon catheter relative to said flexible catheter; said rotational mechanism includes an alignment component that engages said hypotube: rotation of said alignment component about a longitudinal axis of said housing is configured to cause said hypotube to rotate about said longitudinal axis of said housing; and wherein rotation of said hypotube causes said balloon catheter to rotate within said flexible catheter; said alignment mechanism is configured to advance a distal end of said hypotube toward and away from said distal end of said housing; said alignment component is an alignment knob arrangement that includes an alignment knob, an inner cap, a gear tooth, and a biasing arrangement; said gear tooth is biased into engagement with the inner cap by said biasing arrangement; an end of said the gear tooth is configured to engage flexible engagement flanges on said inner cap to cause said flexible engagement flanges to engage an outer surface of said hypotube or sleeve about said hypotube; said alignment mechanism is configured to advance a distal end of said hypotube toward and away from said distal end of said housing only when said switch is in said unlocked position; said alignment mechanism is configured to rotate said hypotube when said switch is in either said locked or unlocked position; said alignment mechanism is configured to advance a distal end of said hypotube toward and away from said distal end of said housing only when said switch is in said unlocked position; said alignment mechanism is configured to only rotate said hypotube when said switch is in said unlocked position.

* * * * *